United States Patent
Jamiluddin et al.

(10) Patent No.: US 10,864,265 B2
(45) Date of Patent: Dec. 15, 2020

(54) LENTIVIRAL VECTORS FOR EXPRESSION OF HEPATITIS B VIRUS (HBV) ANTIGENS

(71) Applicant: THERAVECTYS, Paris (FR)

(72) Inventors: Mohamad Jamiluddin, Frederick, MD (US); Ana Bejanariu, Boulogne-Billancourt (FR); Emeline Sarry, Malakoff (FR)

(73) Assignee: THERAVECTYS, Paris (FR)

( * ) Notice: Subject to any disclaimer, the term of this patent is extended or adjusted under 35 U.S.C. 154(b) by 0 days.

(21) Appl. No.: 16/320,772

(22) PCT Filed: Jul. 20, 2017

(86) PCT No.: PCT/EP2017/068412
§ 371 (c)(1),
(2) Date: Jan. 25, 2019

(87) PCT Pub. No.: WO2018/019705
PCT Pub. Date: Feb. 1, 2018

(65) Prior Publication Data
US 2019/0160166 A1    May 30, 2019

(30) Foreign Application Priority Data

Jul. 27, 2016  (EP) ..................... 16305976

(51) Int. Cl.
*A61K 39/29* (2006.01)
*A61P 31/14* (2006.01)
*C12N 15/86* (2006.01)
*A61K 39/00* (2006.01)

(52) U.S. Cl.
CPC ............ *A61K 39/29* (2013.01); *A61K 39/292* (2013.01); *A61P 31/14* (2018.01); *C12N 15/86* (2013.01); *A61K 2039/5256* (2013.01); *A61K 2039/5258* (2013.01); *C07K 2319/00* (2013.01); *C12N 2740/15011* (2013.01); *C12N 2740/15043* (2013.01); *C12N 2740/16011* (2013.01); *C12N 2740/16043* (2013.01); *C12N 2799/027* (2013.01); *C12N 2840/203* (2013.01)

(58) Field of Classification Search
None
See application file for complete search history.

(56) References Cited

FOREIGN PATENT DOCUMENTS

WO    2008/103380 A2    8/2008
WO    2016/120492 A1    8/2016

OTHER PUBLICATIONS

Jamiluddin et al: "Lentiviral-Based Novel Bicistronic Therapeutic Vaccine against Chronic Hepatitis B Induces Robust Immune Response", International Journal of Medical and Health Sciences—Conference: World Academy of Science, Engineering and Technology, at London, vol. International Journal of Health Sciences, vol. 2, No. 9, p. 937, 2015.
Depla et al: "Rational Design of a Multiepitope Vaccine Encoding T-Lymphocyte Epitopes for Treatment of Chronic Hepatitis B Virus Infections", Journal of Virology, The American Society for Microbiology, US, vol. 82, No. 1, pp. 435-450, Jan. 1, 2008.
Ding et al: "Multiepitope peptide-loaded virus-like particles as a vaccine against hepatitis B virus-related hepatocellular carcinoma", Hepatology, vol. 49, No. 5, pp. 1492-1502, May 6, 2009.
Karwacz et al: "Nonintegrating Lentivector Vaccines Stimulate Prolonged T-Cell and Antibody Responses and Are Effective in Tumor Therapy", Journal of Virology, vol. 83, No. 7, pp. 3094-3103, Jan. 28, 2009.
Hong et al: "Lentivector expressing HBsAg and immunoglobulin Fc fusion antigen induces potent immuno responses and results in seroconversion in HBsAg transgenic mice", Vaccine Elsevier Ltd, GB, vol. 20, No. 22, pp. 3909-3916, Mar. 8, 2011.

*Primary Examiner* — Nicole Kinsey White
(74) *Attorney, Agent, or Firm* — W&C IP

(57) ABSTRACT

The invention relates to nucleic acids, including lentiviral vectors and lentiviral vector particles, encoding at least one Hepatitis B virus (HBV) envelop surface of genotypes A and/or C antigen, at least one polymerase of genotypes A and/or C antigen, at least one HBX protein of genotypes A and/or C antigen, at least one HBV consensus core of genotypes A and/or C antigen, and at least one HBV consensus core MHCI and MHCII epitopes of genotypes A and/or C antigen. The invention encompasses these lentiviral vectors and lentiviral vector particles, methods of making the vectors, and their use, including medicinal uses. The lentiviral vectors and lentiviral vector particles are for use in administering to humans to induce immune responses against the HBV antigens.

17 Claims, 2 Drawing Sheets

Specification includes a Sequence Listing.

- HBV-3: HBV VLP vaccine upstream to IRES and HBV T-cell epitope vaccine down stream to IRES.

FIGURE 1

LENTIVIRAL VECTORS FOR EXPRESSION OF HEPATITIS B VIRUS (HBV) ANTIGENS

TECHNICAL FIELD

The present invention is in the field of recombinant vaccine technology and relates to improvements of lentiviral vectors, which can be used as therapeutic and prophylactic vaccines. The vectors provide improved induction of immune responses over other vectors.

BACKGROUND

Recombinant vaccines have been developed with the progress of recombinant DNA technology, allowing the modification of viral genomes to produce modified viruses. In this manner, it has been possible to introduce genetic sequences into non-pathogenic viruses, so that they encode immunogenic proteins to be expressed in target cells upon infection or transduction, in order to develop a specific immune response in their host.

Such vaccines constitute a major advance in vaccine technology (Kutzler et al., Nat Rev Genet, 9(10): 776-788, 2008). In particular, they have the advantage over traditional vaccines of avoiding live (attenuated) virus and eliminating risks associated with the manufacture of inactivated vaccines.

Gene delivery using modified retroviruses (retroviral vectors) was introduced in the early 1980s by Mann et al. (*Cell,* 33(1):153-9, 1983). The most commonly used oncogenic retroviral vectors are based on the Moloney murine leukemia virus (MLV). They have a simple genome from which the polyproteins Gag, Pol and Env are produced and are required in trans for viral replication (Breckpot et al., 2007, *Gene Ther,* 14(11):847-62; He et al. 2007, *Expert Rev vaccines,* 6(6):913-24). Sequences generally required in cis are the long terminal repeats (LTRs) and its vicinity: the inverted repeats (IR or att sites) required for integration, the packaging sequence ψ, the transport RNA-binding site (primer binding site, PBS), and some additional sequences involved in reverse transcription (the repeat R within the LTRs, and the polypurine tracts, PPT, necessary for plus strand initiation). To generate replication-defective retroviral vectors, the gag, pol, and env genes are generally entirely deleted and replaced with an expression cassette.

Retroviral vectors deriving from lentivirus genomes (i.e. lentiviral vectors) have emerged as promising tools for both gene therapy and immunotherapy purposes, because they exhibit several advantages over other viral systems. In particular, lentiviral vectors themselves are not toxic and, unlike other retroviruses, lentiviruses are capable of transducing non-dividing cells, in particular dendritic cells (He et al. 2007, *Expert Rev vaccines,* 6(6):913-24), allowing antigen presentation through the endogenous pathway.

Lentiviruses are linked by similarities in genetic composition, molecular mechanisms of replication and biological interactions with their hosts. They are best known as agents of slow disease syndromes that begin insidiously after prolonged periods of subclinical infection and progress slowly; thus, they are referred to as the "slow" viruses (Narayan et al., 1989, *J Gen Virol,* 70(7):1617-39). They have the same basic organization as all retroviruses but are more complex due to the presence of accessory genes (e.g., vif, vpr, vpu, nef, tat, and rev), which play key roles in lentiviral replication in vivo.

Lentiviruses represent a genus of slow viruses of the Retroviridae family, which includes the human immunodeficiency viruses (HIV), the simian immunodeficiency virus (SIV), the equine infectious encephalitis virus (EIAV), the caprine arthritis encephalitis virus (CAEV), the bovine immunodeficiency virus (BIV) and the feline immunodeficiency virus (FIV). Lentiviruses can persist indefinitely in their hosts and replicate continuously at variable rates during the course of the lifelong infection. Persistent replication of the viruses in their hosts depends on their ability to circumvent host defenses.

The design of recombinant integrating lentiviral vectors is based on the separation of the cis- and trans-acting sequences of the lentivirus. Efficient transduction in non-dividing cells requires the presence of two cis-acting sequences in the lentiviral genome, the central polypurine tract (cPPT) and the central termination sequence (CTS). These lead to the formation of a triple-stranded DNA structure called the central DNA "flap", which maximizes the efficiency of gene import into the nuclei of non-dividing cells, including dendritic cells (DCs) (Zennou et al., 2000, Cell, 101(2) 173-85; Arhel et al., 2007, *EMBO J,* 26(12): 3025-37).

Dendritic cells are of primary importance for antigen presentation because they constitute the main class of antigen presenting cells (APCs) whose primary function is to present antigens and initiate an immune response.

To generate an immune response, antigenic proteins must be processed by cells into peptides that are displayed on the cell surface by major histocompatibility complex proteins (MHCs). Circulating APCs present the peptide-MHC complexes to T cells in the draining lymph nodes, where they interact with T cell receptors, and, in conjunction with co-stimulatory signals, activate the T cells.

A variety of studies have shown that inoculation with lentiviral vectors leads to antigen presentation by DCs and strong activation of antigen specific cytotoxic T lymphocytes (CTLs; $CD8^+$ T cells). Therefore, lentiviral vectors have been engineered for the last 10 years for gene transfer and immunotherapy applications.

The vectors routinely contain strong constitutive promoters containing enhancers, such as the CMV promoter. Michelini et al., Vaccine 27(34):4622-29 (2009); Karwacz et al., J. Virol. 83(7):30943103 (2009); Negri et al., Molecular Therapy 15(9):1716-23 (2007); and Buffa et al., J. General Virology 87:1625-1634 (2006).

Lentiviral vectors have been improved in their safety by removal of the LTR U3 sequence, resulting in "self-inactivating" vectors that are entirely devoid of viral promoter and enhancer sequences originally present within the LTRs.

The lentiviral particles, which contain lentiviral vectors, can be produced by recombinant technology upon transient transfection of cells, for example HEK 293T human cultured cells, by different DNA plasmids:

(i) a packaging plasmid, which expresses at least the Gag, Pol Rev, Tat and, in some cases, structural and enzymatic proteins necessary for the packaging of the transfer construct;

(ii) a proviral transfer plasmid, containing an expression cassette and HIV cis-acting factors necessary for packaging, reverse transcription, and integration; and (iii) an envelope-encoding plasmid, in most cases the glycoprotein of vesicular stomatitis virus (VSV.G), a protein that allows the formation of mixed particles (pseudotypes) that can target a wide variety of cells, especially major histocompatibility (MHC) antigen-presenting cells (APCs), including DCs.

This procedure allows obtaining transient production of lentiviral particle vectors by the transfected cells. However, the lentiviral particle vectors may also be continuously produced by cells by stably inserting the packaging genes, the proviral coding DNA, and the envelope gene into the cellular genome. This allows the continuous production of lentiviral particle vectors by the cells without the need for transient transfection. Of course, a combination of these procedures can be used, with some of the DNAs/plasmids integrated into the cellular genome and others provided by transient transfection.

Non-integrating lentiviral vectors have been designed to mitigate the risks of potential oncogenesis linked to insertional mutagenesis events, particularly for vaccination purposes. Examples of non-integrating lentiviral vectors are provided in Coutant et al., PLOS ONE 7(11):e48644 (2102), Karwacz et al., J. Virol. 83(7):3094-3103 (2009), Negri et al., Molecular Therapy 15(9):1716-1723 (2007); Hu et al., Vaccine 28:6675-6683 (2010). Consequently, it has been reported that a non-integrating lentiviral vector system can mitigate the potential risk of insertional mutagenesis as compared to an integrating system. Hu et al., Vaccine 28:6675-6683 (2010). It has been further reported that in some functional analysis, both the magnitude and quality of the immune responses elicited by DC-directed integration-defective lentiviral vectors (IDLVs) are comparable to that of its integrating counterpart. Id. Thus, integration-defective lentiviral vectors (IDLVs) have been considered safer vectors than integrating vectors for human administration, with comparable effectiveness.

In addition, deletion in the U3 region of the 3' LTR of the viral promoter and enhancer sequences in self-inactivating lentiviral vectors limits the likelihood of endogenous promoter activation. These concerns with safety directly address the experiences gained from the SCID-X1 gene therapy trial carried out in 1998-1999, performed with Moloney virus-based retroviral vectors on children suffering from a rare form of X-linked (SCID-X1 gene) severe immunodeficiency disease (Cavazzana-Calvo et al., 2000, Science., 288(5466):669-72). During this trial, four of nine children developed leukemia as a result of the integration of the Moloney-derived retroviral vector at close proximity to the human LM02 proto-oncogene (Hacein-Bey-Abina et al., 2008, J. Clin. Invest., 118(9):3132-3142). It was demonstrated that malignancy was the consequence of the proximity of the viral U3 promoter/enhancer to the LM02 proto-oncogene. As a result, safety is a major concern for the administration of lentivectors to humans.

Enhancers are cis-acting sequences, which can act as transcriptional activators at a distance. They have been widely employed in viral derived vectors because they appear to be the most efficient for obtaining transgene strong expression in a variety of cell types, in particular DCs (Chinnasamy et al., 2000, Hum Gene Ther 11(13):1901-9; Rouas et al., 2008, Cancer Gene Ther 9(9):715-24; Kimura et al., 2007, Mol Ther 15(7):1390-9; Gruh et al., 2008, J Gene Med 10(1) 21-32). However, given the safety issue of insertional mutagenesis, such transcriptional enhancer sequences should be deleted from the lentiviral vector constructs to abolish the risk of insertional mutagenesis by enhancer proximity effect. This enhancer proximity effect is by far the most frequent mechanism of insertional mutagenesis and is the only effect described in human or animal cases of tumorigenic events after gene transfer.

Thus, there is a need to develop retroviral, particularly lentiviral vectors, which do not include viral enhancers, but still allow sufficient expression of transgenes encoding immunogenic peptides, if possible, as much expression as that observed when using the CMV promoter.

Recent studies has reported on the replacement of viral promoters by DC-specific promoters deriving from major histocompatibility complex class II genes (MHC class II) (Kimura et al., 2007, Mol Ther 15(7):1390-9) and dectin-2 genes (Lopes et al., 2008, J Virol 82(1):86-95). The dectin-2 gene promoter used in Lopes et al. contains a putative enhancer and an adenoviral conserved sequence (inverted terminal repeats in adenovirus promoter) (Bonkabara et al., 2001, J. Immunology, 167:6893-6900). The MHC class II gene promoter used by Kimura et al. does not contain any known enhancer.

Yet, without an enhancer, the MHC class II promoter was found not to provide sufficient transgene expression in DCs, when administered intravenously. In particular, lentiviral vectors including MHC class II promoters did not provoke an immune reaction in immunocompetent C57BL/6 mice, in contrast to the immune responses observed with CMV promoters/enhancers. Although integration and persistent transgene expression were observed after injection in mice, the lentiviral vectors transcribed through MHC class II promoters failed to stimulate an antigen-specific CD8+ cytotoxic T-lymphocyte response, even after vaccination boost. The authors of these studies therefore concluded that the use of MHC class II promoters was of interest only for applications where persistence of expression is sought as in gene replacement therapy, but not in the context of immunotherapy. Of note, MHC class II promoters are expressed poorly in most cell types.

Thus, the MHC class II promoter is not an adequate promoter for lentiviral vectors for induction of an immune response against an antigen via IV injection. Moreover, the dectin-2 promoter is expressed poorly in most cell types and appears to contain an enhancer. Thus, the dectin-2 promoter is not a good promoter for lentiviral vectors for safety reasons.

Preferably, in immunotherapy, lentiviral vectors provide effective expression of the transgene that elicits a desired specific immune response. This requires that the expression is at a high level in APCs, such as dendritic cells.

It is also preferable that the cells transduced by the lentiviral vectors are eliminated by the immune response to provide a higher degree of safety. That is, the immune response generated against the transgene can elicit an immune response in the host sufficient to eliminate the cells that are transduced by the lentiviral vectors. The elimination of transduced cells eliminates the persistence of the lentiviral vector in the host, and possible secondary effects of the vector. In order for the transduced cells to be eliminated, expression is required in non-dendritic cells at a level that allows elimination by the immune response. Thus, appropriate expression of an antigen is desirable.

At the same time, the promoter should maximize immune stimulation through the key cells (i.e., dendritic cells) involved in the activation of naïve and memory T cells, and should minimize the risk of insertional mutagenesis and genotoxicity in stem cells, leading to malignancies. Thus, the promoter should have sufficiently high activity in dendritic and other cells, but not contain an enhancer. Based on these criteria, viral promoters, such as the CMV promoter, are not ideal because of the presence of strong enhancers. These criteria are summarized as follows:

1. high expression in antigen presenting cells, including dendritic cells, to induce maximal immune responses;
2. expression in other transduced cell types sufficient for elimination by the induced immune response; and
3. lack of an enhancer element to avoid insertional effects.

Hepatitis B is a serious and common viral infectious disease of the liver, more than 2 000 million people alive today have been infected with HBV at some time in their lives. 350 million remain infected chronically and three quarters of the world's population live in areas where there are high levels of infection (Fatusi et al., East African Medical Journal 2000; 77 (11): 608-612).

The severe pathological consequences of persistent HBV infections include the development of chronic hepatic insufficiency cirrhosis and hepatocellular carcinoma (HCC). HBV carriers, can transmit the disease for many years. Chronic HBV (CHB) has been associated with 100-fold increase in risk for development of hepatocellular carcinoma (HCC) (Beasley et al., Lancet. 1981; 2:1129-1133). It is estimated that 15-40% of CHB patients develop cirrhosis or HCC in their lifetimes, contributing to more than 1 million deaths every year (Mast et al., Vaccine, vol. 17, no. 13-14, pp. 1730-1733, 1999; McQuillan et al., American Journal of Public Health, vol. 89, no. 1, pp. 14-18, 1999.). Even though effective prophylactic vaccine has been available for over three decades, HBV still remains among the 10 leading causes of deaths worldwide. Current FDA approved treatments have limited efficacy (Foundation HB. Approved drugs for Adults. (In). Hepatitis B Foundation: Doylestown, Pa., USA, 2012).

To treat chronic HBV disease, antiviral compounds targeting HBV polymerase are in use (Scaglione et al., Gastroenterology 2012; 142: 1360-1368; de Clercq et al., Viruses 2010; 2: 1279-1305).

The weakness of therapy is patients seldom establish immunologic control over HBV, response is rarely durable, patients can experience relapse of disease after years of treatment, HBV replication levels rebounds to pretreatment levels once the treatment stopped, more importantly, treatment failure is common in patients. Toxic effects of long-term treatments enhances the risk of selecting HBV strains resistant to drugs and often economically unaffordable (de Clercq et al., Viruses 2010; 2: 1279-1305; Tong S, et al., Emerg Microbes Infect 2013; 2: e10).

The current prophylactic HBV vaccine, which targets the HBsAg of the virus is effective in inducing protective antibodies following three vaccination routines. There are still 370 million people who are chronically infected and are in need of effective therapies. Prophylactic vaccines are ineffective at already infected HBV carriers or hepatitis patients. Prophylactic vaccines show diminished therapeutic efficacy, due to exhaustive T-cell response against HBsAg and HBs Ab cannot eliminate intracellular hepatocyte HBV (Shen et al., Vaccine 2010; 28: 7288-7296; Chen et al., Clin Vaccine Immunol 2011; 18: 1789-1795). Some of the major challenges facing current vaccine candidates are the inability to induce both humoral and CMI to multiple antigenic targets and induction of potent immune responses against the major genotypes of HBV.

Immunotherapy with PEGylated IFN-α leads to significant adverse reactions and low tolerability (Lok et al., Hepatology 45: 507-539). Therefore, novel therapeutic approaches to combat HBV are urgently needed.

Therapeutic vaccination presents a promising strategy in approach towards HBV eradication. During the past several years, different therapeutic vaccines have been developed and investigated in patients with different clinical outcomes (Kapoor et al., Future Virol. 2014; 9(6):565-585). Vaccines based on recombinant HBV proteins, HBV-envelope subviral particles, viral and plasmid DNA are being developed (id.). Therapeutic vaccination used concomitantly with antiviral agents to induce T-cell restoration with suppression of viral replication and antigen load could provide improvement in vaccine efficacy (id.).

An efficient multispecific anti-HBV immune response induced to resolve chronic HBV infection could be achieved by therapeutic vaccination. If effective, it may circumvent long-term therapy and possible treatment failure due to antiviral resistance or side effects. Immunotherapies intend to trigger either nonspecific or HBV-specific immune responses could limit viral load after appropriate partial treatment (Protzer et al., Nat RevImmunol 2012; 12(March (3)):201-13). Support for the efficacy of T-cells has been gained from the clinical observation that chronic HBV infection may resolve in bone marrow transplant patients receiving bone marrow from an HBV immune donor (Ilan et al., Gastroenterology 1993; 104(June (6)):1818-21). Nearly all the current vaccine candidates facing major challenges due to their inability to induce both humoral and cellular immunity to various antigenic targets and the stimulation of potent immune responses against the major genotypes of HBV. T cell responses could be induced by therapeutic vaccination, and preclinical studies in chimpanzees showed a promising outcome (Schirmbeck et al., Biol Chem 1999; 380(March (3)):285-91; Pancholi et al., Hepatology 2001; 33(February (2)):448-54).

Clinical studies with prophylactic vaccines, alone or in combination with interferon-alpha and/or antiviral compounds were not able to induce an immune response in chronic hepatitis B (Heintges et al., Dig Dis Sci 2001; 46(April (4)):901-6; Hilleman et al., Vaccine. 2003; 21(December 32)):4626-49). It was reasoned that failure was mainly due to aluminum adjuvanted vaccines induce a pronounced Th2 type immune response and do not stimulate CTL.

HBcAg 18-27 HLA-A2 peptide epitope vaccine, lipopeptide Theradigm®, and universal tetanus toxoid helper T cell epitope elicited a CTL response in healthy volunteers, but had no therapeutic effect in chronic HBV patients (Vitiello et al., J Clin Invest 1995; 95(January (1)):341-9; Heathcote et al., Hepatology 1999; 30(August (2)):531-6).

Adjuvants MPL, QS21 and an oil-in water emulsion with HBsAg induced specific T cells and antibodies in healthy volunteers (Vandepapeliere et al., Vaccine 2008; 26 (March (10)):1375-86), but in patients with HBeAg positive chronic HBV under lamivudine treatment unsuccessful to increase HBeAg seroconversion rates (Xu et al., PLoS One 2008; 3(7):e2565). HBsAg complexed with anti-HBs also showed only minor effects in clinical studies (Id.).

Only single HBV antigen was included in the vaccine in all these approaches. In addition, particulate antigens (e.g. virus-like particles) combined with a potent adjuvant appear better suited to induce robust CD4+ and CD8+ T-cell responses.

Incorporating the more immunogenic pre-S domains of the M and L HBV envelope proteins into vaccine formulations as well as using different HBsAg subtypes may be a choice to induce more effective B- and T-cell responses (Milich et al., Science 228: 1195-1199 (1985); Schirmbeck et al., Eur J Immunol 33: 3342-3352 (2003); Schumann et al., J Viral Hepat 14: 592-598 (2007)).

Development of protein-based vaccination has been accomplished by combining HBsAg with HBcAg, as the latter is known to have exceptional immunogenic properties. HBcAg is able to augment priming of T cells through activation of B cells permitting them to act as effective primary antigen presenting cells (Milich et al., Proc Natl Acad Sci USA 94: 14648-14653 (1997); Lazdina et al., J Virol 75: 6367-6374 (2001)).

Moreover, it can trigger Toll-like receptor (TLR-) signaling through nucleic acids bound to its arginine-rich region (Aguilar et al., Immunol Cell Biol 82: 539-546 (2004); Storni et al., J Immunol 172: 1777-1785 (2004)). HBcAg is thus qualified for use as a potent adjuvant when aiming to generate HBV-specific T cells as well as T cells towards heterologous antigen, e.g. HCV or tumor-derived antigens (Chen et al., J Immunol 186: 5107-5118 (2011)).

Viral and antigen load reduction prior to vaccination using antiviral compounds offers a potential improvement of vaccine efficacy. Inhibition of viral replication through nucleos(t)ide analogues can lead to transient CD4+ T-cell responses in chronic hepatitis B patients (Boni et al., J Clin Invest 102: 968-975 (1998)).

Additional evidence for sustained therapeutic effects of combined antiviral treatment and vaccination has been gained in the woodchuck model (Menne et al., J Virol 76: 5305-5314 (2002); Roggendorf et al., Pathol Biol (Paris) 58: 308-314 (2010)).

Instead of co-administration, it is effective to use antiviral pre-treatment prior to vaccination to reduce the antigen load which is a probable cause for tolerance induction (Horiike et al., J Clin Virol 32: 156-161 (2005)).

In chronically HBV-infected patients, taken together, vaccination approaches combining HBsAg and the highly immunogenic HBcAg are a promising strategy to reduce viral load and induce sero conversion.

The synergistic effect of HBsAg and HBcAg should be exploited to stimulate broad and strong HBV-specific B- and T-cell responses to cut antigenic load and to break existing immune tolerance in chronically HBV-infected patients.

Series of different therapeutic vaccination strategies have been attempted using different animal models (i.e. HBV-transgenic mice, woodchuck hepatitis virus model or chronically HBV infected chimpanzees) (Kosinska et al., Hepat Res Treat 2010: 817580 (2010)).

Several of those strategies have reached clinical development stages with different outcomes (Beckebaum et al., Rev Med Virol 12: 297-319 (2002); Akbar et al., Antivir Ther 15: 887-895 (2010); Michel et al., J Hepatol 54: 1286-1296 (2011)).

Preferably, one would generate vaccines that have all the characteristics of wild type with the exception of pathogenic properties. Important features of pathogens that can be mimicked by vaccine delivery systems are their size, shape and surface molecule organization. In addition, pathogen related molecular patterns can be added to promote innate immune responses that activate adaptive immunity (Bachmann et al., Nat Rev Immunol 10: 787-796 (2010)).

Epitope-based vaccines represent a dominant method to stimulate broadly directed immune responses against conserved epitopes from a number of antigens without the use of intact gene products which may have unknown or pathogenic properties.

Studies from numerous laboratories, including our own, have shown that vaccines encoding minimal CTL epitopes can concurrently induce responses against multiple epitopes. So far, therapeutic vaccine candidates for HBV have focused on the use of HBsAg and core proteins or parts thereof (Bienzle et al., Hepatology 38: 811-819 (2003); Jung et al., Vaccine 20:3598-3612 (2002); Livingston et al., J. Immunol. 162:3088-3095 (1999); Pol et al., J. Hepatol. 34:917-921 (2001); Schneider et al., J. Hepatol. 44(Suppl. 2):5277 (2006)).

However, cellular immune responses to these antigens probably are most prone to suppression, tolerance, or other dysfunctions, since these proteins circulate in very high levels in the infected host (Kakimi et al., J. Virol. 76:8609-8620 (2002); Reignat et al., J. Exp. Med. 195:1089-1101 (2002)). The effectiveness of HBV core antigens in eliciting strong cellular immunity in small animals, NHPs and humans, and the therapeutic effect of antibodies against HBV envelop suggest that a combination approach has importance (Kosinska A D et al., J Virol 2012; 86: 9297-9310. Huang Z H et al., World J Gastroenterol 2001; 102: 6. Livingston B D et al., Hum Immunol 1999; 60: 1013-1017). Recently, it has been shown that recombinant protein vaccine using combination approach has been safe and immunogenic-eliciting antibodies to HBV envelop and core antigenic targets in a phase I/II human trial (Cassidy A et al., Expert Rev Vaccines. 2011; 10: 1709-1715).

Hitherto the polymerase antigen has not been as comprehensively investigated as therapeutic vaccine candidate, even though the immune system may be more likely to respond to this antigen, which is produced only in tiny amounts compared to production of the HBsAg and core antigen. Importantly, polymerase-specific CTL and CD4+ helper responses can be readily detected in patients recovering from HBV infection. Chronic patients treated antiviral drugs restored HBV polymerase and core-specific T cell responses during the first year of treatment, but subsequently, responses declined and, after 3 years, were no different than in untreated patients (Mizukoshi et al., J. Immunol. 173:5863-5871 (2004)).

Multifunctional regulatory protein HBV X protein (HBx) may participate in viral pathogenesis and carcinogenesis (Su et al., Proc Natl Acad Sci USA 1997; 94:8744-8749). HBx was highly expressed in hepatitis and hepatoma tissues, it may be a target for immunotherapy to induce specific CTL responses.

The significance of antibodies to HBV cure is reinforced by the correlation of decrease in viral load with presence of anti-HBs and anti-HBe antibodies in HBV-infected patients. The seroconversion that protects 85% of individuals immunized with the current HBV vaccine is also an indication of the role of antibodies in protection against HBV. However, due to its intracellular nature HBV may still progress to disease in the presence of high titer antibodies and thus cellular immunity likely is crucial in clearing the infection.

Therapeutic vaccine, which induces cellular immune responses along with significant B cell responses implicated in protection, would likely be important to target HBV in treatment protocols.

Thus, a need exists in the art for improved vectors and methods for immunizing humans. The present invention fulfills these needs in the art.

SUMMARY OF THE INVENTION

The invention encompasses nucleic acid molecules and vectors encoding:
- at least one Hepatitis B virus (HBV) envelop surface of genotypes A and/or C antigen,
- at least one polymerase of genotypes A and/or C antigen,
- at least one HBX protein of genotypes A and/or C antigen,
- at least one HBV consensus core of genotypes A and/or C antigen, and
- at least one HBV consensus core MHCI and MHCII epitopes of genotypes A and/or C antigen,
- and their use as a medicament or vaccine.

Preferably, the vector of the invention is a lentiviral vector.

In particular, the present invention concerns a lentiviral vector encoding:
- at least one Hepatitis B virus (HBV) envelop surface of genotypes A and/or C antigen,
- at least one polymerase of genotypes A and/or C antigen,
- at least one HBX protein of genotypes A and/or C antigen,
- at least one HBV consensus core of genotypes A and/or C antigen, and
- at least one HBV consensus core MHCI and MHCII epitopes of genotypes A and/or C antigen.

In a preferred embodiment, a lentiviral vector of the invention encodes at least the amino acid sequence of SEQ ID NO: 24.

In a preferred embodiment, a lentiviral vector of the invention encodes at least the amino acid sequence of SEQ ID NO: 25.

In a particularly preferred embodiment, a lentiviral vector of the invention encodes at least the amino acid sequence of SEQ ID NO: 24 and at least the amino acid sequence of SEQ ID NO: 25.

In one embodiment, the lentiviral vector of the invention comprises a β2-microglobulin promoter.

In one embodiment, the lentiviral vector of the invention comprises a Woodchuck PostTranscriptional Regulatory Element (WPRE).

In one embodiment, the lentiviral vector of the invention is a DNA.

The invention further encompasses a lentiviral vector particle encoding:
- at least one Hepatitis B virus (HBV) envelop surface of genotypes A and/or C antigen,
- at least one polymerase of genotypes A and/or C antigen,
- at least one HBX protein of genotypes A and/or C antigen,
- at least one HBV consensus core of genotypes A and/or C antigen, and
- at least one HBV consensus core MHCI and MHCII epitopes of genotypes A and/or C antigen.

In a preferred embodiment, the vector of a lentiviral vector particle of the invention encodes at least the amino acid sequence of SEQ ID NO: 24.

In a preferred embodiment, the vector of a lentiviral vector particle of the invention encodes at least the amino acid sequence of SEQ ID NO: 25.

In a particularly preferred embodiment, the vector of a lentiviral vector particle of the invention encodes at least the amino acid sequence of SEQ ID NO: 24 and at least the amino acid sequence of SEQ ID NO: 25.

In one embodiment, the lentiviral vector particle comprises a functional lentiviral integrase protein.

In one embodiment, the lentiviral vector particle comprises a vesicular stomatitis virus glycoprotein.

In one embodiment, the lentiviral vector particle comprises HIV-1 subtype D Gag and Pol proteins.

The invention also encompasses an isolated cell comprising a lentiviral vector of the invention or a lentiviral vector particle of the invention.

The invention further encompasses a lentiviral vector or a lentiviral vector particle according to the invention for use as a medicament or vaccine.

The text also describes the use of a lentiviral vector of the invention or of a lentiviral vector particle of the invention for inducing an immune response in a human, in particular by intramuscular administration.

The text also describes a method for inducing an immune response in a human comprising administering, preferably intramuscularly, a lentiviral vector of the invention or a lentiviral vector particle of the invention to a human.

BRIEF DESCRIPTION OF THE DRAWINGS

FIG. 1 depicts a lentiviral vectored HBV vaccine construct HBV-3 according to the invention. This construct comprises the amino acid sequence of SEQ ID NO:24 (HBV Genotype A & C Surface, Pol, HBX and consensus Core MHCI and MHCII epitopes sequence) and the amino acid sequence of SEQ ID NO:25 (Chimeric VLP with Surface B cell epitopes of genotype A&C sequence).

Figure 2:
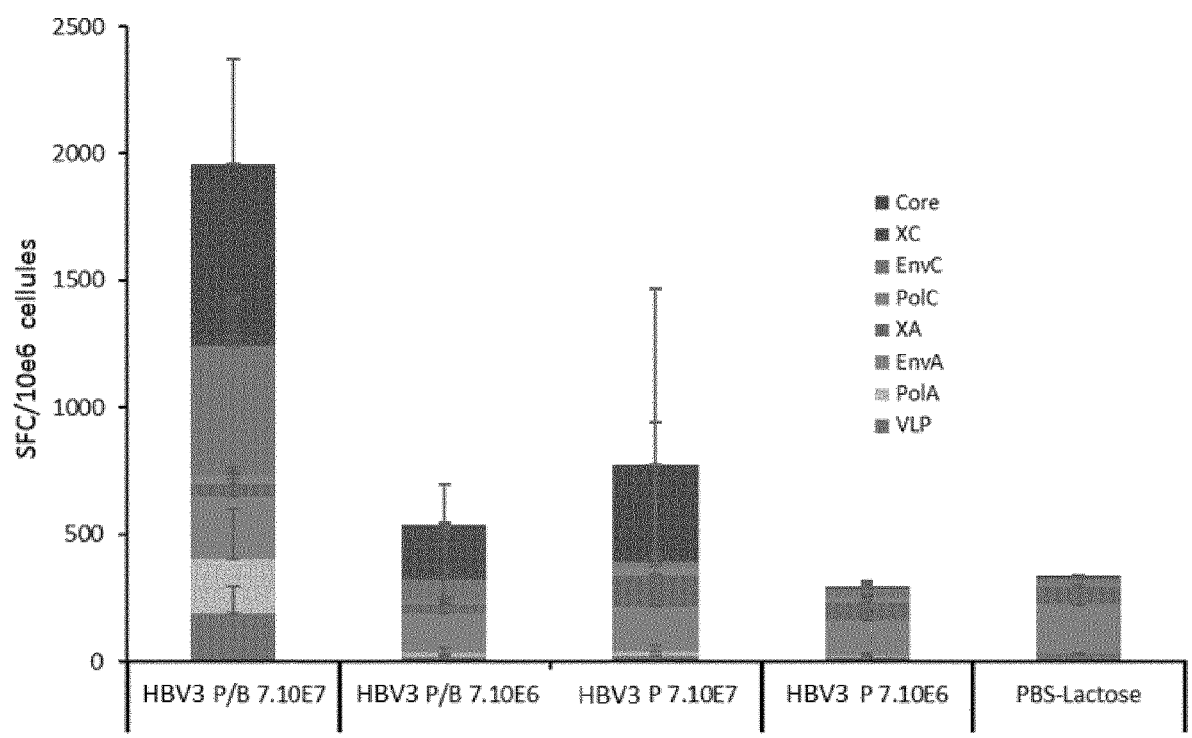
FIG. 2 depicts cumulated immune response and diversity of the T-cell response (IFN-γ secretion) in C57Bl/6j mice with the HBV-3 lentiviral vector.

Different doses of injected lentiviral vectors are compared ($1 \cdot 10^7$ TU and $1 \cdot 10^6$ TU) as well as different administration strategies (prime/boost (P/B) or prime (P)). From the bottom to the top of each bar: VLP, PolA, EnvA, XA, PoIC, EnvC, XC and Core. A and C are HBV genotypes.

DETAILED DESCRIPTION OF THE INVENTION

The inventors have discovered that the intramuscular administration to an animal of a lentiviral vector encoding an antigen results in a high immune response against the protein and can lead to elimination of the integrated vector from the animal. Thus, the invention provides for new lentivectors having high immune responses and increased safety for human administration.

The present invention encompasses lentiviral vectors encoding:
- at least one Hepatitis B virus (HBV) envelop surface of genotypes A and/or C antigen,
- at least one polymerase of genotypes A and/or C antigen,
- at least one HBX protein of genotypes A and/or C antigen,
- at least one HBV consensus core of genotypes A and/or C antigen, and
- at least one HBV consensus core MHCI and MHCII epitopes of genotypes A and/or C antigen, and their use for the induction of immune responses in a host, preferably in a human being, in particular by intramuscular administration.

Lentiviral vectors can enable the induction of a strong, lasting and broad cell-mediated response and humoral response. LVs can incorporate multi-antigenic cassettes allowing the development of multivalent vaccines in a single dose. Filovirus outbreaks occur unexpectedly and spread rapidly. Thus, under these settings, short vaccine regimens may be required. Due to high expression levels of the inserts and the tropism for dendritic cells, THVs Lentiviral vectored vaccines can elicit strong immune responses in short period. Conversely, long-term protective immunity will likely involve a prime-boost regimen consisting of two or more injections that can induce durable T-cell memory.

Proteins

The invention encompasses lentiviral vector constructions encoding proteins comprising at least one:
- at least one Hepatitis B virus (HBV) envelop surface of genotypes A and/or C antigen,
- at least one polymerase of genotypes A and/or C antigen,
- at least one HBX protein of genotypes A and/or C antigen,
- at least one HBV consensus core of genotypes A and/or C antigen, and
- at least one HBV consensus core MHCI and MHCII epitopes of genotypes A and/or C antigen.

Preferably, the at least one hepatitis B virus (HBV) envelop surface of genotypes A and/or C antigen is inserted in the at least one HBV consensus core of genotypes A and/or C antigen, thus forming a chimeric protein. More preferably, said chimeric protein comprises or consists in the amino acid sequence SEQ ID NO: 25.

The HBV consensus core MHCI and MHCII epitopes of genotypes A and/or C antigen consists of different MHCI and MHCII epitopes of core HBV fused and/or linked to one another by short linking sequences, preferably via a short sequence of two amino acids GS, and preferably comprises or consists in the amino acid sequence SEQ ID NO: 26:

```
                                          (SEQ ID NO: 26)
MDIDPYKEFGATVELLSFLPSDFFPSVRDLGSALESPEHCSPHHTALRQA

ILGSELMTLATWVGSSRDLVVNYVNTNMGLKIRQLLWFHISCLTFGRETV

LEYLVSFGVWIRTPPGSILSTLPETTVVRRRDRGRSPRRRT.
```

Preferably, the at least one polymerase of genotypes A and/or C antigen, the at least one HBX protein of genotypes A and/or C antigen, and the at least one HBV consensus core MHCI and MHCII epitopes of genotypes A and/or C antigen are comprised in or form the amino acid sequence SEQ ID NO: 24.

Preferably, the at least one polymerase of genotypes A and/or C antigen according to the invention is at least one polymerase of genotype A and at least one polymerase of genotype C.

Preferably, the at least one HBX protein of genotypes A and/or C antigen according to the invention is at least one HBX protein of genotype A and at least one HBX protein of genotype C.

Preferably, the at least one Hepatitis B virus (HBV) envelop surface of genotypes A and/or C antigen according to the invention is at least one Hepatitis B virus (HBV) envelop surface of genotype A and at least one Hepatitis B virus (HBV) envelop surface of genotype C.

In a preferred embodiment:
- the at least one polymerase of genotypes A and/or C antigen according to the invention is at least one polymerase of genotype A and at least one polymerase of genotype C;
- the at least one HBX protein of genotypes A and/or C antigen according to the invention is at least one HBX protein of genotype A and at least one HBX protein of genotype C; and
- the at least one Hepatitis B virus (HBV) envelop surface of genotypes A and/or C antigen according to the invention is at least one Hepatitis B virus (HBV) envelop surface of genotype A and at least one Hepatitis B virus (HBV) envelop surface of genotype C.

HBV Genotype A & C Surface, Pol, HBX and core MHC I and MHCII epitopes sequence:

```
                                          (SEQ ID NO: 24)
MWPAANQVGVGAFGPGLGSMQWNSTAFHQALQDPRVRGLGSSISARTGDP

VGSVLQAGFFLLTRILTIPQSLDSWWTSLNFLGGSPVCLGQNSQSPTSNH

SPTSCPPICPGYRWMCLRRFGSIIFLFILLLCLIFLLVLLDYQGMLGSCT

TPAQGNSMFPSCCCTKPTDGNGSIPSSWAFAGSRFSWLSLLVPFVQWFVG

LSPTVWLSAIWMMWYWGPSLYSIVSPFIPLLPIFFCLWVYIGSNVSIPWT

HKVGNFTGLYSSTVPIGSVGPLTVNEKRRLKLIGSRHYLHTLWKAGILYK

GSTPARVTGGVFGSESRLVVDFSQFSRGITRVSWPKFAVPNLQSLTNLLS
```

-continued

```
SNLSWLSLDVSAAFYHIPLHPAAMPHLLIGSSGLSRYVARLGSLHLYSHP

IVLGFRKIGSSAICSVVRRAFPHCLAFSYMDDVVLGAGSFLLSLGIHLGS

KHCFRKLPVNRPIDWGSYPALMPLYACIQAKQAFTFSPTYKAFLSGSLCQ

VFADATPTGWGLGSKYTSFPWLLGCTANWILRGTSFVYVPGSSLYAVSPS

VHLSLRGLPVGSVLHKRTLGLPAMSTTDLGSCVFKDWEELGEEIRLKVLF

VLGGCRHKLGSWPEANQVGAGAFGPGFGSMQWNSTTFHQALLDPRVRGLY

FPAGGSSSGGSTSLNFLGGAPTCPGQGSCTIPAQGTSMFPSCCCTKPSDG

NCTCGSGLSPTVWLSVIWMMWYWGPSLYNILSPFLPLLPIFFCLWVYIGS

NVSIPWTHKVGNFTGLYSSTVPVGSLHLYSHPIILGFRKIGSKQCFRKLP

VNRPIDWGSKQAFTFSPTYKAFLCGSLCQVFADATPTGWGLGSAANWILR

GTSFVYVPGSVLHKRTLGLSAMSTTDLGSCLFKDWEELGEEIRLMIFVLG

GCRHKLGSMDIDPYKEFGATVELLSFLPSDFFPSVRDLGSALESPEHCSP

HHTALRQAILGSELMTLATWVGSSRDLVVNYVNTNMGLKIRQLLWFHISC

LTFGRETVLEYLVSFGVWIRTPPGSILSTLPETTVVRRRDRGRSPRRRT.
```

Chimeric VLP with Surface B cell epitopes sequence of genotype A&C:

```
                                          (SEQ ID NO: 25)
MDIDPYKEFGATVELLSFLPSDFFPSVRDLLDTASALYREALESPEHCSP

HHTALRQAILCWGELMTLATWVGNNLEDGGGGSGGGGTPLGFFPDHQLDP

AFGANSNNPDWDFNGSASTNRQSGRQPTPISPPLRDSHPQMQWNSTAFHQ

ALQDPRVRGLYFPAGGSSSGTVNPAPNIASHISSISARTGDGSCKTCTTP

AQGNSMFPSCCCTKPTDGNCTCIPIPSSWAFAKYLWEWASGSPFVQWFVG

LAMQWNSTTFHQALLDPRVRGLYFPAGGSSSGTVNPVPTTASPISSIFSR

TGDGSCKTCTIPAQGTSMFPSCCCTKPSDGNCTCIPIPSSWAFARFLWEW

ASGSGGGGSGGGGSRDLVVNYVNTNMGLKIRQLLWFHISCLTFGRETVLE

YLVSFGVWIRTPPAYRPPNAPILSTLPETTVVRRRDRGRSPRRRTPSPRR

RRSQSPRRRRSQSRESQC.
```

The proteins can be purified.

Preferably, the purified protein is more than 50%, 75%, 85%, 90%, 95%, 97%, 98%, or 99% pure. Within the context of this invention, a purified protein that is more than 50% (etc.) pure means a purified protein sample containing less than 50% (etc.) other proteins. For example, a sample of a recombinant protein purified from a host cell can be 99% pure if it contains less than 1% contaminating host cell proteins.

Nucleic Acids

The invention encompasses nucleic acids encoding:

- at least one Hepatitis B virus (HBV) envelop surface of genotypes A and/or C antigen,
- at least one polymerase of genotypes A and/or C antigen,
- at least one HBX protein of genotypes A and/or C antigen,
- at least one HBV consensus core of genotypes A and/or C antigen, and
- at least one HBV consensus core MHCI and MHCII epitopes of genotypes A and/or C antigen.

The nucleic acid can be single-stranded or double-stranded. The nucleic acid can be an RNA or DNA molecule.

Preferred nucleic acids encode an amino acid sequence of any of the SEQ ID NOs detailed herein, either alone or combined, such as SEQ ID NO:24 and SEQ ID NO:25. The invention encompasses an isolated nucleic acid of the invention inserted into a vector.

The nucleic acid can be purified. Preferably, the purified nucleic acid is more than 50%, 75%, 85%, 90%, 95%, 97%, 98%, or 99% pure. Within the context of this invention, a purified nucleic acid that is more than 50% pure means a purified nucleic acid sample containing less than 50% other nucleic acids. For example, a sample of a plasmid purified from a host bacteria can be 99% pure if it contains less than 1% contaminating bacterial DNA.

Preferably, the at least one polymerase of genotypes A and/or C antigen encoded by a nucleic acid according to the invention is at least one polymerase of genotype A and at least one polymerase of genotype C.

Preferably, the at least one HBX protein of genotypes A and/or C antigen encoded by a nucleic acid according to the invention is at least one HBX protein of genotype A and at least one HBX protein of genotype C.

Preferably, the at least one Hepatitis B virus (HBV) envelop surface of genotypes A and/or C antigen encoded by a nucleic acid according to the invention is at least one Hepatitis B virus (HBV) envelop surface of genotype A and at least one Hepatitis B virus (HBV) envelop surface of genotype C.

In a preferred embodiment:
the at least one polymerase of genotypes A and/or C antigen encoded by a nucleic acid according to the invention is at least one polymerase of genotype A and at least one polymerase of genotype C;
the at least one HBX protein of genotypes A and/or C antigen encoded by a nucleic acid according to the invention is at least one HBX protein of genotype A and at least one HBX protein of genotype C; and
the at least one Hepatitis B virus (HBV) envelop surface of genotypes A and/or C antigen encoded by a nucleic acid according to the invention is at least one Hepatitis B virus (HBV) envelop surface of genotype A and at least one Hepatitis B virus (HBV) envelop surface of genotype C.

Vectors

The invention encompasses vectors encoding:
at least one Hepatitis B virus (HBV) envelop surface of genotypes A and/or C antigen,
at least one polymerase of genotypes A and/or C antigen,
at least one HBX protein of genotypes A and/or C antigen,
at least one HBV consensus core of genotypes A and/or C antigen, and
at least one HBV consensus core MHCI and MHCII epitopes of genotypes A and/or C antigen, and preferably comprising a SEQ ID of the invention.

Preferably, the at least one polymerase of genotypes A and/or C antigen encoded by a vector, in particular a lentiviral vector, according to the invention is at least one polymerase of genotype A and at least one polymerase of genotype C.

Preferably, the at least one HBX protein of genotypes A and/or C antigen encoded by a vector, in particular a lentiviral vector, according to the invention is at least one HBX protein of genotype A and at least one HBX protein of genotype C.

Preferably, the at least one Hepatitis B virus (HBV) envelop surface of genotypes A and/or C antigen encoded by a vector, in particular a lentiviral vector, according to the invention is at least one Hepatitis B virus (HBV) envelop surface of genotype A and at least one Hepatitis B virus (HBV) envelop surface of genotype C.

In a preferred embodiment:
the at least one polymerase of genotypes A and/or C antigen encoded by a vector, in particular a lentiviral vector, according to the invention is at least one polymerase of genotype A and at least one polymerase of genotype C;
the at least one HBX protein of genotypes A and/or C antigen encoded by a vector, in particular a lentiviral vector, according to the invention is at least one HBX protein of genotype A and at least one HBX protein of genotype C; and
the at least one Hepatitis B virus (HBV) envelop surface of genotypes A and/or C antigen encoded by a vector, in particular a lentiviral vector, according to the invention is at least one Hepatitis B virus (HBV) envelop surface of genotype A and at least one Hepatitis B virus (HBV) envelop surface of genotype C.

Preferred vectors comprise a nucleic acid sequence encoding an amino acid sequence of any of the SEQ ID NOs detailed herein, either alone or combined, and in particular SEQ ID NO:24 and/or SEQ ID NO:25, preferably SEQ ID NO:24 and SEQ ID NO:25.

The vector can be an expression vector. The vector can be a plasmid vector. Preferably, the vector is a lentiviral vector.

Within the context of this invention, a "lentiviral vector" means a non-replicating vector for the transduction of a host cell with a transgene comprising cis-acting lentiviral RNA or DNA sequences, and requiring lentiviral proteins (e.g., Gag, Pol, and/or Env) that are provided in trans. The lentiviral vector lacks expression of functional Gag, Pol, and Env proteins. The lentiviral vector may be present in the form of an RNA or DNA molecule, depending on the stage of production or development of said retroviral vectors.

The lentiviral vector can be in the form of a recombinant DNA molecule, such as a plasmid. The lentiviral vector can be in the form of a lentiviral vector particle, such as an RNA molecule(s) within a complex of lentiviral and other proteins. Typically, lentiviral particle vectors, which correspond to modified or recombinant lentivirus particles, comprise a genome which is composed of two copies of single-stranded RNA. These RNA sequences can be obtained by transcription from a double-stranded DNA sequence inserted into a host cell genome (proviral vector DNA) or can be obtained from the transient expression of plasmid DNA (plasmid vector DNA) in a transformed host cell.

Preferably the lentiviral vector particles have the capacity for integration. As such, they contain a functional integrase protein.

Non-integrating vector particles have one or more mutations that eliminate most or all of the integrating capacity of the lentiviral vector particles. For, example, a non-integrating vector particle can contain mutation(s) in the integrase encoded by the lentiviral pol gene that cause a reduction in integrating capacity. In contrast, an integrating vector particle comprises a functional integrase protein that does not contain any mutations that eliminate most or all of the integrating capacity of the lentiviral vector particles.

Lentiviral vectors derive from lentiviruses, in particular human immunodeficiency virus (HIV-1 or HIV-2), simian immunodeficiency virus (SIV), equine infectious encephalitis virus (EIAV), caprine arthritis encephalitis virus (CAEV), bovine immunodeficiency virus (BIV) and feline immunodeficiency virus (FIV), which are modified to remove genetic determinants involved in pathogenicity and introduce new determinants useful for obtaining therapeutic effects.

Such vectors are based on the separation of the cis- and trans-acting sequences. In order to generate replication-defective vectors, the trans-acting sequences (e.g., gag, pol, tat, rev, and env genes) can be deleted and replaced by an expression cassette encoding a transgene.

Efficient integration and replication in non-dividing cells generally requires the presence of two cis-acting sequences at the center of the lentiviral genome, the central polypurine tract (cPPT) and the central termination sequence (CTS). These lead to the formation of a triple-stranded DNA structure called the central DNA "flap", which acts as a signal for uncoating of the pre-integration complex at the nuclear pore and efficient importation of the expression cassette into the nucleus of non-dividing cells, such as dendritic cells.

In one embodiment, the invention encompasses a lentiviral vector comprising a central polypurine tract and central termination sequence referred to as cPPT/CTS sequence as described, in particular, in the European patent application EP 2 169 073.

Further sequences are usually present in cis, such as the long terminal repeats (LTRs) that are involved in integration of the vector proviral DNA sequence into a host cell genome. Vectors may be obtained by mutating the LTR sequences, for instance, in domain U3 of said LTR (ΔU3) (Miyoshi H et al, 1998, *J Virol.* 72(10):8150-7; Zufferey et al., 1998, *J Virol* 72(12):9873-80) as shown in FIG. 1.

Preferably, the vector does not contain an enhancer. In one embodiment, the invention encompasses a lentiviral vector comprising LTR sequences, preferably with a mutated U3 region (ΔU3) removing promoter and enhancer sequences in the 3' LTR.

The packaging sequence ψ (psi) can also be incorporated to help the encapsidation of the polynucleotide sequence into the vector particles (Kessler et al., 2007, *Leukemia*, 21(9):1859-74; Paschen et al., 2004, *Cancer Immunol Immunother* 12(6):196-203).

In one embodiment, the invention encompasses a lentiviral vector comprising a lentiviral packaging sequence ψ (psi).

Further additional functional sequences, such as a transport RNA-binding site or primer binding site (PBS) or a Woodchuck Post Transcriptional Regulatory Element (WPRE), can also be advantageously included in the lentiviral vector polynucleotide sequence of the present invention, to obtain a more stable expression of the transgene in vivo.

In one embodiment, the invention encompasses a lentiviral vector comprising a PBS. In one embodiment, the invention encompasses a lentiviral vector comprising a WPRE and/or an IRES.

Thus, in a preferred embodiment, the lentiviral vector comprises at least one cPPT/CTS sequence, one ψ sequence, one (preferably 2) LTR sequence, and an expression cassette including a transgene under the transcriptional control of a β2m or class I MHC promoter.

Promoter

In various embodiments, the promoter drives high expression in antigen presenting cells, including dendritic cells, to induce maximal immune responses. Preferably, the promoter drives expression in other transduced cell types sufficient for elimination by the induced immune response. Most preferably, the promoter lacks an enhancer element to avoid insertional effects.

Most preferably, the promoter is not a CMV promoter/enhancer. Preferably, the promoter is not a dectin-2 or MHCII promoter.

The sequences of various mammalian (human) MHC class I promoters are shown below:

HLA-A2 (MHC I):
(SEQ ID NO: 1)
attggggagtcccagccttggggattccccaactccgcagtttcttttct ccctctcccaacctatgtagggtccttcttcctggatactcacgacgcgg acccagttctcactcccattgggtgtcgggtttccagagaagccaatcag tgtcgtcgcggtcgcggttctaaagtccgcacgcacccacc gggactcag attctccccagacgccgagg HLA-B7 (MHC I):
(SEQ ID NO: 2)
ggggaggcgcagcgttggggattccccactcccctgagtttcacttcttc tcccaacttgtgtcgggtccttcttccaggatactcgtgacgcgtcccca cttcccactcccattgggtattggatatctagagaagccaatcagcgtcg ccgcggtcccagttctaaagtccccacgcacccacccggactcagag HLA-Cw5 (MHC I):
(SEQ ID NO: 3)
cactggggaggcgccgcgttgaggattctccactcccctcagtttcactt cttctcccaacctgcgtcgggtccttcttcctgaatactcatgacgcgtc cccaattcccactcccattgggtgtcgggttctagagaagccaatcagcg tctccgcagtcccggtctaaagtcccagtcacccacccggactcagatt ctccccagacgccgag HLA-E (MHC I):
(SEQ ID NO: 4)
taagaactgctgattgctgggaaactctgcagtttcccgttcctctcgta acctggtcatgtgtccttcttcctggatactcatgacgcagactcagttc tcattcccaatgggtgtcgggtttctagagaagccaatcagcgtcgccac gactcccgactataaagtccccatccggactcaagaagttctcaggactc agagg HLA-F (MHC I):
(SEQ ID NO: 5)
aggccccgaggcggtgtctggggttggaaggctcagtattgagaattccc catctccccagagtttctctttctctcccaacccgtgtcaggtccttcat cctggatactcataacgcggccccatttctcactcccattgggcgtcgcg tttctagagaagccaatcagtgtcgccgcagttcccaggttctaaagtcc cacgcacccgcgggactcatattttcccagacgcggaggttggggtca tg A sequence of the human β2-microglobulin promoter is shown below:

(SEQ ID NO: 6)
Aacatcacgagactctaagaaaaggaaactgaaaacgggaaagtccctct ctctaacctggcactgcgtcgctggcttggagacaggtgacggtccctgc gggccttgtcctgattggctgggcacgcgtttaatataagtggaggcgtc gcgctggcgggcattcctgaagctgacagcattcgggccgag.

The MHCI and β2m promoters do not contain an enhancer. Moreover, these promoters are dendritic-specific (APCs) in that expression of the promoter in BDCA+ dendritic cells is higher than the expression in kidney, smooth muscle, liver, and heart cells. They also have relatively high expression in other transduced cell types, for example, expression of the promoter in BDCA+ dendritic cells is only 12-100 times the expression of that promoter in skeletal muscle cells, in contrast to 900 times with the MHCII HLA-DRα promoter. Id.

In various embodiments, the lentiviral vector comprises a β2m or MHC class I promoter. Preferably, the MHC class I promoter is an HLA-A2 promoter, an HLA-B7 promoter, an HLA-Cw5 promoter, an HLA-F, or an HLA-E promoter. In various embodiments, the promoter sequence comprises a polynucleotide sequence that shares more than 90%, preferably more than 95%, more preferably more than 99% identity with the promoter sequence of SEQ ID NO:1, SEQ ID NO:2, SEQ ID NO:3, SEQ ID NO:4, SEQ ID NO:5, or SEQ ID NO:6.

The invention encompasses dendritic cell-specific promoters. A "dendritic cell-specific promoter" is one in which expression of the promoter in BDCA+ dendritic cells is higher than the expression in kidney, smooth muscle, liver, and heart cells. Preferably, expression of the promoter in BDCA+ dendritic cells is at least 2×, 3×, or 4× higher than the expression in kidney, smooth muscle, liver, and/or heart cells. Whether a promoter is "(2×, 3×, or 4×) higher than the expression in kidney, smooth muscle, liver, and/or heart cells" can be determined by reference to the data sets at http://biogps.org, which are hereby incorporated by reference or by the use of the Affimetrix probes, chips, and methods used to generate these data sets (particularly HG-U133 set). The β2m, HLA-A2, HLA-B7, HLA-Cw5, HLA-F, and HLA-E promoters are "dendritic cell-specific promoters." The EF1α promoter is not. Thus, preferably the promoter is not an EF1α promoter.

Preferably, the promoter drives expression in other transduced cell types, such as kidney, smooth muscle, liver, and/or heart cells, and skeletal muscle. Preferably, the expression of the promoter in BDCA+ dendritic cells is 12-100 times the expression of that promoter in skeletal muscle cells. Whether "the expression of the promoter in BDCA+ dendritic cells is 12-100 times the expression of that promoter in skeletal muscle cells" can be determine by reference to the data sets at http://biogps.org, which are hereby incorporated by reference or by the use of the Affimetrix probes, chips, and methods used to generate these data sets (particularly HG-U133 set). Most preferably, the expression of the promoter in BDCA+ dendritic cells is 12-100 times the expression of that promoter in skeletal muscle cells and expression of the promoter in BDCA+ dendritic cells is higher than the expression in kidney, smooth muscle, liver, and heart cells. The β2m, HLA-A2, HLA-B7, HLA-Cw5, HLA-F, and HLA-E promoters are promoters where expression of the promoter in BDCA+ dendritic cells is 12-100 times the expression of that promoter in skeletal muscle cells. The HLA-A2 promoter and UBC promoter are not. Thus, preferably the promoter is not an HLA-A2 (MHCII) promoter or UBC (Ubiquitin) promoter.

In some embodiments, the expression of the promoter in BDCA+ dendritic cells is at least 10, 12, 15, 20, 25, 30, 35, 40, 50, or 60 times the expression of that promoter in skeletal muscle cells.

In one embodiment, the invention encompasses lentiviral vector particles comprising a lentiviral vector that comprises a dendritic cell-specific promoter directing expression of at least one Hepatitis B virus (HBV) envelop surface antigen, polymerase, HBX protein and HBV consensus core of genotypes A and C antigen, wherein the lentiviral vector particles exhibit higher expression of the antigen in BDCM cells than in HEK 293 T cells.

In various embodiments, the lentiviral vector comprising the promoter induces a greater CTL response in vivo against the encoded immunogenic polypeptide than a vector in which the transgene sequence is under the transcriptional control of a CMV promoter. Within the context of this invention, whether a vector "induces a greater CTL response in vivo against the encoded immunogenic polypeptide than a vector in which the transgene sequence is under the transcriptional control of a CMV promoter" can be determined using the assay set forth in the examples. Other assays that provide similar results can also be used.

In various embodiments, the lentiviral vector comprising the promoter induces a greater CTL response in vivo against the encoded immunogenic polypeptide than a vector in which the transgene sequence is under the transcriptional control of an EF1α promoter. Preferably, the CTL response with the promoter is at least 2-fold or 3-fold higher than with the EF1α promoter. Within the context of this invention, whether a vector "induces a greater CTL response in vivo against the encoded immunogenic polypeptide than a vector in which the transgene sequence is under the transcriptional control of an EF1α promoter" can be determined using the assay set forth in the examples. Other assays that provide similar results can also be used.

In various embodiments, the lentiviral vector comprising the promoter induces a greater CTL response in vivo against the encoded immunogenic polypeptide than a vector in which the transgene sequence is under the transcriptional control of an Ubiquitin promoter. Within the context of this invention, whether a vector "induces a greater CTL response in vivo against the encoded immunogenic polypeptide than a vector in which the transgene sequence is under the transcriptional control of an Ubiquitin promoter" can be determined using the assay set forth in the examples. Other assays that provide similar results can also be used.

The invention encompasses lentiviral vectors containing a promoter that does not contain an enhancer.

The invention encompasses the insertion of an MHC Class I (MHCI) or β2 microglobulin promoter (β2m) promoter into a lentiviral vector. As used herein, an "MHC Class I (MHCI) promoter" or "β2 microglobulin promoter" includes a naturally occurring or synthetic MHC Class I promoter or β2 microglobulin promoter. The term "MHC Class I promoter" does not include a β2m promoter.

In one embodiment, the lentiviral vector particles comprising the promoter exhibit higher expression of the antigen in BDCM cells than in HEK 293 T cells.

The promoter can be a naturally occurring promoter. Examples of naturally occurring promoters are the human β2m, HLA-A2, HLA-B7, HLA-Cw5, HLA-E, HLA-F gene promoters. These naturally occurring MHCI promoters are generally cloned or reproduced from the promoter region of a gene encoding the MHC class I protein, or referred to as putatively encoding such proteins in genome databases (ex: NCBI polynucleotide database http://www.ncbi.nlm.nih.gov/guide/dna-rna). Both β2m and class I MHC proteins enter the Major Histocompatibility Complex (MHC).

The proteins encoded by these genes are found in almost all cell types. MHCI proteins are generally present at the surface of the membrane of leucocytes, where they are associated with the β2-microglobulin (β2m). The role of these associated proteins is to present peptides from endogenous sources to CD8+ T cells. They thus play a central role to the generation of the antigen-specific immune response. Because MHC class I proteins have been widely studied and described for many years, their genes are well characterized and detectable using sequence comparison tools, such as the BLAST method (Altschul, S. F. et al. (1990). Basic local alignment search tool. *J. Mol. Biol.* 215(3):403-410).

MHC class I promoters share the ability to be strongly activated in antigen presenting cells, including dendritic cells, as well as, to lower intensity, in the majority of the other human body tissues.

The promoters of the invention can contain further regulatory elements, such as one or more Sp1 and ETs binding sites. In a preferred embodiment, the MHC class I promoter contains 2 Sp1 binding sites and 1 Ets binding site. In other embodiments, Ap1 and/or Ap2 sites are further contained in the promoter.

Preferred promoters are naturally occurring human β2m, HLA-A2, HLA-B7, HLA-Cw5, HLA-E and HLA-F promoters.

Promoters can also be synthetic. Synthetic promoters include promoters that are synthesized using molecular biological techniques to assemble the individual components of a promoter or that are derived from naturally occurring promoters using molecular biological techniques.

In various embodiments, the synthetic promoter comprises a polynucleotide sequence that shares more than 90%, preferably more than 95%, more preferably more than 99% identity, or 100% with the promoter sequence of a β2m or MHC class I gene promoter (e.g., SEQ ID NOs: 1-6 and 19).

The transcription of MHC class genes are usually mediated by two major regulatory elements: Interferon stimulated response element (ISRE) and the SXY module (encompassing the W/S, X1X2/Site α and Y/enhancer B regulatory elements) (see FIG. 1). See also Van den Elsen, Immunogenetics (1998) 48:208-211.

These regulatory promoter elements are localized in a region extending approximately from nucleotides −220 to −95 upstream of the transcription initiation site. They mediate tissue-specific and cytokine-induced transcription of MHC class I genes.

The ISRE of MHC class I gene promoters generally contains binding sites for interferon regulatory factor (IRF) family members. It is thus a property of MHC class I promoters to bind to interferon regulatory factor (IRF) family members. This may be verified, for example, by gel shift assays.

Another regulatory element, the enhancer A (containing binding sites for nuclear transcription factor κB (NF-κB)) is present in most cases. It is thus a property of MHC class I promoters to bind to nuclear transcription factor κB (NF-κB). This may be verified, for example, by gel shift assays.

In addition to ISRE, MHC class I promoters generally share another set of conserved upstream sequence motifs, consisting of three regulatory elements: the S or W box, the X1/CREX2 boxes or site α, and the Y box or enhancer B, which together are termed the SXY module. This SXY module is generally cooperatively bound by a multiprotein complex containing regulatory factor X (RFX; consisting of RFX5, RFXB/ANK and RFXAP), cAMP response element binding protein (CREB)/activating transcription factor (ATF), and nuclear factor Y (NFY), which acts as an enhanceosome driving transactivation of these genes. It is thus a property of MHC class I promoters to bind to these factors. This may be verified, for example, by gel shift assays.

In contrast, MHC class II promoters do not display enhancer A nor ISRE elements (Van den Elsen, P. J. et al, 1998, *Immunogenetics*. 48:208-221). Furthermore, RFX and CIITA in MHC class II gene regulation have been found of crucial importance as illustrated by studies with cell lines established from patients with the bare lymphocyte syndrome (BLS), a severe combined immunodeficiency due to mutations in one of the RFX subunits or CIITA (DeSandro, A. et al., 1999, *Am J Hum Genet*, 65:279-286). Also, lack of either CIITA or one of the RFX subunits affects the functioning and assembly of the MHC enhanceosome, respectively, leading to a lack of MHC class II and reduced levels of MHC class I transcription (Van den Elsen, P. J. et al. 2004, *Current Opinion in Immunology*, 16:67-75).

In one embodiment, the invention encompasses a method comprising inserting a promoter of the invention, particularly a β2m or MHC class I promoter, into a lentiviral vector to direct expression of a transgene, which preferably encodes an immunogenic polypeptide, most preferably encoding at least one Hepatitis B virus (HBV) envelop surface antigen, polymerase, HBX protein and HBV consensus core of genotypes A and C antigen. The method can further comprise inserting any of the other nucleic acid elements mentioned herein, such as a DNA flap sequence.

Isolated Cells

The invention encompasses cells comprising vectors and lentiviral vector particles encoding:
- at least one Hepatitis B virus (HBV) envelop surface of genotypes A and/or C antigen,
- at least one polymerase of genotypes A and/or C antigen,
- at least one HBX protein of genotypes A and/or C antigen,
- at least one HBV consensus core of genotypes A and/or C antigen, and
- at least one HBV consensus core MHCI and MHCII epitopes of genotypes A and/or C antigen.

In one embodiment, the cell contains the vector integrated into the cellular genome.

In one embodiment, the cell contains the vector transiently expressing the at least one Hepatitis B virus (HBV) envelop surface of genotypes A and/or C antigen, at least one polymerase of genotypes A and/or C antigen, at least one HBX protein of genotypes A and/or C antigen, at least one HBV consensus core of genotypes A and/or C antigen, and at least one HBV consensus core MHCI and MHCII epitopes of genotypes A and/or C antigen.

In one embodiment, the cell produces lentiviral vector particles encoding the at least one Hepatitis B virus (HBV) envelop surface of genotypes A and/or C antigen, at least one polymerase of genotypes A and/or C antigen, at least one HBX protein of genotypes A and/or C antigen, at least one HBV consensus core of genotypes A and/or C antigen, and at least one HBV consensus core MHCI and MHCII epitopes of genotypes A and/or C antigen.

In various embodiments, the invention encompasses a cell line, a population of cells, or a cell culture comprising vectors and lentiviral vector particles according to the invention.

Preferably, the at least one polymerase of genotypes A and/or C antigen encoded by a vector, in particular a lentiviral vector, or lentiviral vector particle according to the invention is at least one polymerase of genotype A and at least one polymerase of genotype C.

Preferably, the at least one HBX protein of genotypes A and/or C antigen encoded by a vector, in particular a lentiviral vector, or lentiviral vector particle according to the invention is at least one HBX protein of genotype A and at least one HBX protein of genotype C.

Preferably, the at least one Hepatitis B virus (HBV) envelop surface of genotypes A and/or C antigen encoded by a vector, in particular a lentiviral vector, or lentiviral vector particle according to the invention is at least one Hepatitis B virus (HBV) envelop surface of genotype A and at least one Hepatitis B virus (HBV) envelop surface of genotype C.

In a preferred embodiment:
the at least one polymerase of genotypes A and/or C antigen encoded by a vector, in particular a lentiviral vector, or lentiviral vector particle according to the invention is at least one polymerase of genotype A and at least one polymerase of genotype C;
the at least one HBX protein of genotypes A and/or C antigen encoded by a vector, in particular a lentiviral vector, or lentiviral vector particle according to the invention is at least one HBX protein of genotype A and at least one HBX protein of genotype C; and
the at least one Hepatitis B virus (HBV) envelop surface of genotypes A and/or C antigen encoded by a vector, in particular a lentiviral vector, or lentiviral vector particle according to the invention is at least one Hepatitis B virus (HBV) envelop surface of genotype A and at least one Hepatitis B virus (HBV) envelop surface of genotype C.

Lentiviral Vector Particles

The present invention provides a method for producing a lentiviral vector particle. A lentiviral vector particle (or lentiviral particle vector) comprises a lentiviral vector in association with viral proteins. The vector is preferably an integrating vector.

In one embodiment, the lentiviral vector particles encode:
at least one Hepatitis B virus (HBV) envelop surface of genotypes A and/or C antigen,
at least one polymerase of genotypes A and/or C antigen,
at least one HBX protein of genotypes A and/or C antigen,
at least one HBV consensus core of genotypes A and/or C antigen, and
at least one HBV consensus core MHCI and MHCII epitopes of genotypes A and/or C antigen.

Preferably, the at least one polymerase of genotypes A and/or C antigen encoded by a lentiviral vector particle according to the invention is at least one polymerase of genotype A and at least one polymerase of genotype C.

Preferably, the at least one HBX protein of genotypes A and/or C antigen encoded by a lentiviral vector particle according to the invention is at least one HBX protein of genotype A and at least one HBX protein of genotype C.

Preferably, the at least one Hepatitis B virus (HBV) envelop surface of genotypes A and/or C antigen encoded by a lentiviral vector particle according to the invention is at least one Hepatitis B virus (HBV) envelop surface of genotype A and at least one Hepatitis B virus (HBV) envelop surface of genotype C.

In a preferred embodiment:
the at least one polymerase of genotypes A and/or C antigen encoded by a lentiviral vector particle according to the invention is at least one polymerase of genotype A and at least one polymerase of genotype C;
the at least one HBX protein of genotypes A and/or C antigen encoded by a lentiviral vector particle according to the invention is at least one HBX protein of genotype A and at least one HBX protein of genotype C; and
the at least one Hepatitis B virus (HBV) envelop surface of genotypes A and/or C antigen encoded by a lentiviral vector particle according to the invention is at least one Hepatitis B virus (HBV) envelop surface of genotype A and at least one Hepatitis B virus (HBV) envelop surface of genotype C.

Preferably, the lentiviral vector particles comprise a nucleic acid sequence encoding an amino acid sequence of any of the SEQ ID NOs detailed herein, either alone or combined, such as SEQ ID NO:24 and/or SEQ ID NO:25, and preferably encoding at least SEQ ID NO: 24 and SEQ ID NO: 25.

In one embodiment, the lentiviral vector particle comprises HIV-1 Gag and Pol proteins. Preferably, the lentiviral vector particle comprises subtype D, especially HIV-1$_{NDK}$, Gag and Pol proteins.

According to one embodiment of this method, the lentivector particles are obtained in a host cell transformed with a DNA plasmid.

Such a DNA plasmid can comprise:
bacterial origin of replication (ex: pUC ori);
antibiotic resistance gene (ex: KanR) for selection; and more particularly:
a lentiviral vector comprising at least one transgene transcriptionally linked to a MHC class I promoter.

Such a method allows producing a recombinant vector particle according to the invention, comprising the following steps of:
i) transfecting a suitable host cell with a lentiviral vector;
ii) transfecting said host cell with a packaging plasmid vector, containing viral DNA sequences encoding at least structural and polymerase (+ integrase) activities of a retrovirus (preferably lentivirus); Such packaging plasmids are described in the art (Dull et al., 1998, *J Virol*, 72(11):8463-71; Zufferey et al., 1998, *J Virol* 72(12):9873-80).
iii) culturing said transfected host cell in order to obtain expression and packaging of said lentiviral vector into lentiviral vector particles; and
iv) harvesting the lentiviral vector particles resulting from the expression and packaging of step iii) in said cultured host cells.

For different reasons, it may be helpful to pseudotype the obtained retroviral particles, i.e. to add or replace specific particle envelope proteins. For instance, this may be advantageous to have different envelope proteins in order to distinguish the recombinant particle from natural particles or from other recombinant particles. In matter of vaccination strategy, pseudotyped particle vectors are more likely to escape the immune system, when this latter already developed immunity against lentiviruses. This is particularly helpful when successive injections of similar particle vectors are required for immunizing a patient against a disease.

In order to pseudotype the retroviral particles of the invention, the host cell can be further transfected with one or several envelope DNA plasmid(s) encoding viral envelope protein(s), preferably a VSV-G envelope protein.

An appropriate host cell is preferably a human cultured cell line as, for example, a HEK cell line.

Alternatively, the method for producing the vector particle is carried out in a host cell, which genome has been stably transformed with one or more of the following components: a lentiviral vector DNA sequence, the packaging genes, and the envelope gene. Such a DNA sequence may be regarded as being similar to a proviral vector according to the invention, comprising an additional promoter to allow the transcription of the vector sequence and improve the particle production rate.

In a preferred embodiment, the host cell is further modified to be able to produce viral particle in a culture medium in a continuous manner, without the entire cells swelling or dying. One may refer to Strang et al., 2005, *J Virol* 79(3): 1165-71; Relander et al., 2005, *Mol Ther* 11(3):452-9;

Stewart et al., 2009, *Gene Ther*, 16(6):805-14; and Stuart et al., 2011, *Hum gene Ther.*, with respect to such techniques for producing viral particles.

An object of the present invention consists of a host cell transformed with a lentiviral particle vector.

The lentiviral particle vectors can comprise the following elements, as previously defined:
cPPT/CTS polynucleotide sequence; and
a transgene sequence under control of a promoter of the invention, and optionally one of the additional elements described above.

Preferably, the lentivector particles are in a dose of $10^6$, $2 \times 10^6$, $5 \times 10^6$, $10^7$, $2 \times 10^7$, $5 \times 10^7$, $10^8$, $2 \times 10^8$, $5 \times 10^8$, or $10^9$ TU.

Methods for Expressing a Transgene in a Cell

The present invention encompasses methods for expressing a transgene in a cell, preferably a non-dividing cell. The method comprises transducing a cell with a lentiviral vector or lentiviral particle vector of the invention under conditions that allow the expression of the transgene.

The cells are preferably mammalian cells, particularly human cells. Particularly preferred are human non-dividing cells.

The transgene preferably encodes at least one Hepatitis B virus (HBV) envelop surface antigen, polymerase, HBX protein and HBV consensus core of genotypes A and C antigen. The method can further comprise harvesting or isolating the polypeptide.

The lentiviral vector or lentiviral particle vector preferably comprises a promoter of the invention.

In one embodiment, the invention encompasses a method for expressing a transgene comprising inserting promoter of the invention into a lentiviral vector such that it direct the expression of a transgene and transducing a cell with the vector containing the promoter.

Therapeutic Use of Lentiviral Vectors

The present invention further relates to the use of the lentiviral vectors according to the invention, especially in the form of lentiviral vector particles, for the preparation of therapeutic compositions or vaccines which are capable of inducing or contributing to the occurrence or improvement of an immunogical reaction against epitopes, more particularly those encoded by the transgene present in the vectors under the transcriptional control of any of the promoters of the invention.

The invention encompasses methods of administration of a lentiviral vector (or "lentivector") to a human. Preferably, the lentivector contains a promoter that drives high expression of an antigen in antigen presenting cells, including dendritic cells, and drives expression in other transduced cell types sufficient for elimination by the induced immune response. Most preferably, the promoter lacks an enhancer element to avoid insertional effects.

Preferably, the administration is intramuscular. In one embodiment, the lentivector is injected into the muscle using a needle.

The antigens according to the invention are:
at least one Hepatitis B virus (HBV) envelop surface of genotypes A and/or C antigen,
at least one polymerase of genotypes A and/or C antigen,
at least one HBX protein of genotypes A and/or C antigen,
at least one HBV consensus core of genotypes A and/or C antigen, and
at least one HBV consensus core MHCI and MHCII epitopes of genotypes A and/or C antigen.

Preferably, the lentivector particle is an integrating lentivector particle, comprising a functional integrase protein.

Most preferably, the administration eliminates at least 95%, 99%, 99.9%, or 99.99% of the lentiviral DNA integrated in the muscle cells of an animal model at day 4 after administration is eliminated by day 21 after administration.

In one embodiment, the invention comprises a method for inducing an immune response in a human comprising intramuscularly administering lentiviral vector particles comprising a functional integrase protein and a lentiviral vector to a human; wherein the integrating lentiviral vector comprises a promoter directing expression of at least one Hepatitis B virus (HBV) envelop surface of genotypes A and/or C antigen, at least one polymerase of genotypes A and/or C antigen, at least one HBX protein of genotypes A and/or C antigen, at least one HBV consensus core of genotypes A and/or C antigen, and at least one HBV consensus core MHCI and MHCII epitopes of genotypes A and/or C antigen, wherein the promoter does not contain an enhancer, and wherein the lentiviral vector particles exhibit higher expression of the antigens in BDCM cells than in HEK 293 T cells; integrating the DNA of the lentiviral vector into cells of the human; expressing the antigens in the cells of the human; and generating an immune response against the antigens.

In one embodiment, the invention comprises a method for inducing an immune response in a human comprising intramuscularly administering lentiviral vector particles comprising a functional integrase protein and a lentiviral vector to a human; wherein the integrating lentiviral vector comprises a promoter directing expression of at least one Hepatitis B virus (HBV) envelop surface of genotypes A and/or C antigen, at least one polymerase of genotypes A and/or C antigen, at least one HBX protein of genotypes A and/or C antigen, at least one HBV consensus core of genotypes A and/or C antigen, and at least one HBV consensus core MHCI and MHCII epitopes of genotypes A and/or C antigen, wherein the promoter does not contain an enhancer, wherein expression of the promoter in BDCA+ dendritic cells is higher than the expression in kidney, smooth muscle, liver, and heart cells; integrating the DNA of the lentiviral vector into cells of the human; expressing the antigens in the cells of the human; and generating an immune response against the antigens.

In one embodiment, the invention comprises a method for inducing an immune response in a human comprising intramuscularly administering lentiviral vector particles comprising a functional integrase protein and a lentiviral vector to a human; wherein the integrating lentiviral vector comprises a promoter directing expression of at least one Hepatitis B virus (HBV) envelop surface of genotypes A and/or C antigen, at least one polymerase of genotypes A and/or C antigen, at least one HBX protein of genotypes A and/or C antigen, at least one HBV consensus core of genotypes A and/or C antigen, and at least one HBV consensus core MHCI and MHCII epitopes of genotypes A and/or C antigen, wherein the promoter does not contain an enhancer, wherein the expression of the promoter in BDCA+ dendritic cells is 12-100 times the expression of that promoter in skeletal muscle cells; integrating the DNA of the lentiviral vector into cells of the human; expressing the antigens in the cells of the human; and generating an immune response against the antigens.

In one embodiment, the invention comprises a method for inducing an immune response in a human comprising intramuscularly administering lentiviral vector particles comprising a functional integrase protein and a lentiviral vector to a human; wherein the integrating lentiviral vector comprises a promoter directing expression of at least one Hepatitis B virus (HBV) envelop surface of genotypes A and/or C antigen, at least one polymerase of genotypes A and/or C antigen, at least one HBX protein of genotypes A and/or C antigen, at least one HBV consensus core of genotypes A and/or C antigen, and at least one HBV consensus core MHCI and MHCII epitopes of genotypes A and/or C antigen, wherein the promoter does not contain an enhancer, wherein expression of the promoter in BDCA+ dendritic cells is higher than the expression in kidney, smooth muscle, liver, and heart cells, and wherein the expression of the promoter in BDCA+ dendritic cells is 12-100 times the expression of that promoter in skeletal muscle cells; integrating the DNA of the lentiviral vector into cells of the human; expressing the antigens in the cells of the human; and generating an immune response against the antigens.

In some embodiments, the method comprises eliminating at least 95%, 99%, 99.9% or 99.99% of the lentiviral DNA integrated in the muscle cells of an animal model at day 4 after administration by day 21, day 25, day 33, or day 66 after administration. Elimination of integrated lentiviral in muscle cells can be measured as described in the examples and by other similar techniques. For example, a biopsy can be taken at the site of the injection of a mouse or rat at 4 days and at 21 days and the amount of integrated DNA in the cells determined at these time points by PCR.

In one embodiment, the invention comprises a method for inducing an immune response in a human comprising intramuscularly administering lentiviral vector particles comprising a functional integrase protein and a lentiviral vector to a human; wherein the integrating lentiviral vector comprises a promoter directing expression of at least one Hepatitis B virus (HBV) envelop surface of genotypes A and/or C antigen, at least one polymerase of genotypes A and/or C antigen, at least one HBX protein of genotypes A and/or C antigen, at least one HBV consensus core of genotypes A and/or C antigen, and at least one HBV consensus core MHCI and MHCII epitopes of genotypes A and/or C antigen, wherein the promoter does not contain an enhancer; integrating the DNA of the lentiviral vector into cells of the human; expressing the antigens in the cells of the human; and generating an immune response.

Preferably, the lentivector particles are in a dose of $10^6$, $2\times10^6$, $5\times10^6$, $10^7$, $2\times10^7$, $5\times10^7$, $10^8$, $2\times10^8$, $5\times10^8$, or $10^9$ TU. More preferably, the lentivector particles are in a dose of at least $1\times10^7$ TU, in particular at least $7\times10^7$ TU.

The immune response induced by the lentiviral vector can be a B cell response, a CD4+ T cell response, and/or a CD8+ T cell response.

The present invention thus provides vectors that are useful as a medicament or vaccine, particularly for intramuscular administration.

These vectors are preferentially for use in the treatment or prophylaxis of infectious diseases, especially diseases associated with virus infection and more particularly, with HBV infection.

As the vectors of the invention more specifically target dendritic cells to obtain a cell-mediated immune response and especially the CTL response associated with the antigen expressed by the transgene in these cells, they are particularly useful as vaccines targeting HBV.

Accordingly, the invention relates to an immunogenic composition comprising a lentiviral vector as previously defined.

The immunogenic compositions of the invention preferably contain cPPT and CTS sequences in the vector and vector particles to induce or to stimulate the nuclear import of the vector genome in the target cells.

During reverse transcription, cPPT and CTS sequences induce the formation of a three stranded DNA structure referred as DNA triplex, which stimulates the nuclear import of DNA vector sequence. Preferably, the vector comprises a transgene and regulatory signals of retrotranscription, expression and encapsidation of retroviral or retroviral-like origin, wherein the composition is capable of inducing or of stimulating a CTL (Cytotoxic T Lymphocytes) and/or a CD4 response against one or several epitopes encoded by the transgene sequence present in the vector.

The expression of the transgene is greatly improved by inclusion of a promoter of the invention in the vector.

Thus, the lentiviral vectors according to the invention have the ability to induce, improve, or in general be associated with the occurrence of a B cell response, a CD4+ T cell response, and/or a CD8+ T cell response, especially a memory CTL response, in particular against HBV. In other words, they can be used for the preparation of therapeutic composition for the treatment of allergies, autoimmune diseases, tumor diseases, or infectious diseases, in particular of HBV, by induction of, stimulation of, or participation in the occurrence of a cell-mediated immune response, especially a CTL response or a memory response.

The lentiviral vectors of the invention can be used in methods of treatment and methods of inducing an immune response, in particular against HBV, comprising administering the lentiviral vector to a host and generating a specific immune response against the transgene in the host. The cells and antibodies generated in these hosts can be used as diagnostic reagents.

The lentiviral vectors according to the invention are preferably for intramuscular administration, most preferably by injection with a needle.

In a particular embodiment, the immunogenic composition according to the invention can be directly administered to the patient, in such a way that it will induce, improve, or participate in vivo in the occurrence of a B cell response, a CD4+ T cell response, and/or a CD8+ T cell response, especially a CTL-mediated immune response, in particular against HBV.

In another embodiment, the immunogenic compositions are used once or upon repeated administration, preferably at least upon two administrations, so that they can enable the occurrence of a long-term memory cell mediated response.

A particular advantage of the immunogenic compositions of the invention is that they can be used to elicit or stimulate a cell-mediated immune response against multiple epitopes encoded by the nucleotides sequence of interest or transgene present in the vector or vector particles, in particular against HBV, and they can also be used to elicit or stimulate a cell-mediated immune response against the product of the entire sequence of a gene.

The invention also encompasses a lentiviral vector comprising a nucleotide sequence encoding a multiple repeat (at least 2 identical sequences) of said amino acid sequence inducing a cellular response and/or an amino acid sequence containing at least 2 different sequences.

As a result, the invention encompasses a composition that could be used in prophylactic and/or therapeutic vaccination protocols, in particular against HBV.

In particular, it can be used in combination with adjuvants, other immunogenic compositions, chemotherapy, or any other therapeutic treatment, in particular against HBV.

The invention encompasses a composition for intramuscular administration to a human comprising lentiviral vector particles comprising a functional integrase protein and a lentiviral vector; wherein the DNA of the lentiviral vector comprises a promoter directing expression of an amino acid comprising or consisting of at least one Hepatitis B virus (HBV) envelop surface of genotypes A and/or C antigen, at least one polymerase of genotypes A and/or C antigen, at least one HBX protein of genotypes A and/or C antigen, at least one HBV consensus core of genotypes A and/or C antigen, and at least one HBV consensus core MHCI and MHCII epitopes of genotypes A and/or C antigen, particularly encoded by an amino acid sequence of any of the SEQ ID NOs detailed herein.

In one embodiment, the invention encompasses a composition for intramuscular administration to a human comprising lentiviral vector particles comprising a functional integrase protein and a lentiviral vector; wherein the DNA of the lentiviral vector comprises a promoter directing expression of an amino acid comprising or consisting of at least one Hepatitis B virus (HBV) envelop surface of genotypes A and/or C antigen, at least one polymerase of genotypes A and/or C antigen, at least one HBX protein of genotypes A and/or C antigen, at least one HBV consensus core of genotypes A and/or C antigen, and at least one HBV consensus core MHCI and MHCII epitopes of genotypes A and/or C antigen, particularly encoded by an amino acid sequence of any of the SEQ ID NOs detailed herein, wherein the promoter does not contain an enhancer, and wherein the expression of the promoter in BDCA+ dendritic cells is 12-100 times the expression of that promoter in skeletal muscle cells and expression of the promoter in BDCA+ dendritic cells is higher than the expression in kidney, smooth muscle, liver, and heart cells.

The invention encompasses use of a composition comprising lentiviral vector particles for intramuscular administration to a human, wherein the lentiviral vector particles comprise a functional integrase protein and a lentiviral vector; wherein the DNA of the lentiviral vector comprises a promoter directing expression of an amino acid comprising or consisting of at least one Hepatitis B virus (HBV) envelop surface of genotypes A and/or C antigen, at least one polymerase of genotypes A and/or C antigen, at least one HBX protein of genotypes A and/or C antigen, at least one HBV consensus core of genotypes A and/or C antigen, and at least one HBV consensus core MHCI and MHCII epitopes of genotypes A and/or C antigen, particularly encoded by an amino acid sequence of any of the SEQ ID NOs detailed herein.

In one embodiment, the invention encompasses use of a composition comprising lentiviral vector particles for intramuscular administration to a human, wherein the lentiviral vector particles comprise a functional integrase protein and a lentiviral vector; wherein the DNA of the lentiviral vector comprises a promoter directing expression of an amino acid comprising or consisting of at least one Hepatitis B virus (HBV) envelop surface of genotypes A and/or C antigen, at least one polymerase of genotypes A and/or C antigen, at least one HBX protein of genotypes A and/or C antigen, at least one HBV consensus core of genotypes A and/or C antigen, and at least one HBV consensus core MHCI and MHCII epitopes of genotypes A and/or C antigen, particularly encoded by an amino acid sequence of any of the SEQ ID NOs detailed herein, wherein the promoter does not contain an enhancer, and wherein the expression of the promoter in BDCA+ dendritic cells is 12-100 times the expression of that promoter in skeletal muscle cells and expression of the promoter in BDCA+ dendritic cells is higher than the expression in kidney, smooth muscle, liver, and heart cells.

Having thus described different embodiments of the present invention, it should be noted by those skilled in the art that the disclosures herein are exemplary only and that various other alternatives, adaptations, and modifications may be made within the scope of the present invention. Accordingly, the present invention is not limited to the specific embodiments as illustrated herein.

EXAMPLES

Example 1. Molecular Constructions

PCR amplification of the proviral region of the pTRIPΔU3-CMV-GFP(15) was performed using direct (5'-CTTACTAGTTGGAAGGGCTAATTCACT CCCAAC-3'; SEQ ID NO: 7) and reverse (5'-CAT-TCTAGAACTGCTAGAG ATTTTCCACACTG-3'; SEQ ID NO: 8) oligonucleotides encompassing respectively the SpeI and XbaI restriction sites. The resulting fragment was digested and cloned between the SpeI and XbaI sites of the pVAX-1 plasmid (Invitrogen, Lifetech) from which the MluI site have been deleted. The resulting plasmid was named pFLAP-CMV-GFP. The SV40 sequence was amplified by PCR from the pTRIPΔU3-CMV-GFP plasmid (using the 5'-TACCCCGGGCCA TGGCCTCCAAAAAAGCCTCCT-CACTACTTC-3' (SEQ ID NO: 9) and 5'-ACTCCCGGGTAATTTTTTTTATT-TATGCAGAGGCCGAG GCCGCC-3' (SEQ ID NO: 10) oligonucleotides), and cloned into the Pml1 site of the pFLAP-CMV-GFP, the resulting plasmid being then named pFLAP-CMV-GFP-SV. The CMV promoter was amplified with direct (5'-TACACGCGTGGAGTTCCGCGTTACATA ACTTACGG-3'; SEQ ID NO: 11) and reverse (5'-CGTG-GATCCGATCGCGGT GTCTTCTATGGAGGTCAAAAC-3'; SEQ ID NO: 12) oligonucleotides encompassing the MluI and BamHI sites, respectively. The resulting fragment was cloned back between the MluI and BamHI sites of the pFlap-CMV-GFP-SV allowing the easy replacement of the promoters inside the lentiviral vectors. The promoter was then amplified by PCR from HEK 293T cells DNA with 5'-GCCGGCGCGCCGAGAAACCCTGCAGGGAAT-TCCC-3' (SEQ ID NO: 13) and 5'-CGTGGATCC-GATCGCTCGGCCCGAATGCTGTCAGCTTCAGG-3' (SEQ ID NO: 14) for the β2m promoter and cloned between the MluI and BamH1 sites of pFLAP-CMV-GFP-SV to create pFlap-β2m-SV. The amplified β2m promoter sequence is the following:

GAGAAACCCTGCAGGGAATTCCCCAGCTGTAGT-TATAAACAGAAGTTC TCCTTCTGCTAGGTAGCATT-CAAAGATCTTAATCTTCTGGGTTTCCGTTTTCTC GAATGAAAAATGCAGGTCCGAGCAGT-TAACTGGCGGGGGCACCATTAGCAA GTCACTTAG-CATCTCTGGGGCCAGTCTGCAAAGCGAGGGGGCA GCCTTAAT GTGCCTCCAGCCTGAAGTCCTAGAAT-GAGCGCCCGGTGTCCCAAGCTGGGG CGCGCACCCCAGATCGGAGGGCGCCGATGTACA-GACAGCAAACTCACCCAG TCTAGTGCATGCCTTCT-TAAACATCACGAGACTCTAAGAAAAGGAAACT-GAAA ACGG-GAAAGTCCCTCTCTCTAACCTGGCACTGCGTCGCT GGCTTGGAGACAG GTGACGGTCCCTGCGGGCCTTGTCCTGAT-TGGCTGGGCACGCGTTAATATA AGTG-GAGGCGTCGCGCTGGCGGGCATTCCT-GAAGCTGACAGCATTCGGGCC GAG (SEQ ID NO:

15). The HBV antigen can be synthetized and cloned between the BamHI and XhoI sites of the pFlap-β2m-SV, in place of the GFP gene.

For example, pFlap-β2m-GFP-SV can be digested by BamHI and XhoI, and a DNA linker containing a Multiple Cloning Site (MCS, carrying SalI, SadI, NdeI, AscI and NheI restriction sites) can be cloned between those sites, in place of the GFP gene to allow insertion of a nucleic acid sequence encoding the HBV antigen.

The packaging plasmid pTHV-GP-N was constructed by amplifying the HIV-NDK genome by PCR (using the following oligonucleotides with 5'-atgcatgcgtcgacctcgagt-taatcctcatcctgtctacttgccac-3' (SEQ ID NO: 16) and 5'-gcatg-catcggccggggcggcgactgGTgagagGCCACCatgggtgcgagagcgtcagt-attaag-3' (SEQ ID NO: 17). The resulting fragment has been digested by EagI and SalI restriction enzymes and inserted in the p8.74 packaging plasmid (15) from which the Eag1-SalI fragment had been previously removed.

Pseudotyping plasmids were generated by synthesizing the codon optimized genes corresponding to the vesicular stomatitis virus Indiana (GenBank # CAX62728.1), New Jersey GenBank # CAX62729.1) and Cocal (GenBank # CAX62731.1) strains. Those genes were then digested with EcoR1 and BamH1 and cloned between the corresponding restriction sites of the pVAX1 plasmid (Invitrogen, Lifetech).

The plasmids can produced using Nucleobond Xtra Maxi EF column according to manufacturer's instructions (Macherey Nagel).

Example 2. Lentiviral Production

R&D productions: Vectors can be produced by transient calcium-phosphate transfection of HEK 293T as previously describe (25).

Preclinical and GMP productions: The day before transfection, HEK 293T cells are seeded in culture medium on 24 units of Cell Factory 10 (CF-10, Nunc). Cells are transfected by a calcium-phosphate method as reported previously (25). 18 to 24 hours post-transfection, culture medium is changed with production medium corresponding to Dubelcco's modified Eagle's medium (DMEM/High modified, Hyclone) supplemented with 2% heat-inactivated fetal calf serum (FCS, PAA), 1% L-Glutamine (Gibco by Life technologies), 1% Penicillin-Streptomycin (Gibco by Life technologies), 1% Sodium Pyruvate (GIBCO Gibco by Life technologies), BENZONASE® (pharma grade 1, 100 000U, Merck Millipore) and $MgCL_2$ 1M. Minimum 24 hours after medium renewal, supernatant of the 24 CF-10 is harvested and pooled. After a second BENZONASE® treatment, supernatant is clarified by filtration on KLEENPAK NOVA PROFILE II cartridge (Pall). After clarification, a third BENZONASE® treatment is applied overnight at +2/+8° C. Viral vector were purified using Anion exchange chromatography on Mustang-Q XT cassette (Pall). Lentiviral particles are eluted in two steps with 0.5M and 1.2M NaCl. Both fractions are diluted to decrease NaCl concentration up to +150 mM before pooling. 1EX eluate is further concentrated approximately 40 fold by ultrafiltration using a 100 KDa Omega T series filter, 0.1 $m^2$ (Pall) and diafiltrated with PBS-Lactose 40 mg·L−1. Purified bulk (Drug substance) is finally filtered through a 0.2 μM Sartobran H5 filter, 300 $cm^2$ (Sartorius Stedim) and aseptically distributed on 2R 3 mL-glass vials with a target filling volume of 6504 (12004 for pilot batches). After visual inspection of all the vials (about 350 vials by clinical batch), drug product is stored at −70° C.±10° C.

For product characterization and pharmaceutical release, quality tests can be performed according to regulatory texts on vaccines: the quality control required for vaccines as per the European Pharmacopeia (section 6.16), the "guideline on quality, non-clinical and clinical aspects of live recombinant viral vectored vaccines" (EMA/CHMP/141697/2009), the "guideline on development and manufacture of lentiviral vectors" (CHMP/BWP/2458/03); regulatory text on gene therapy medicinal products: the quality controls required for gene transfer medicinal products for human use as per the European Pharmacopeia (section 5.14), the quality controls specific to gene therapy products as defined in the "note for guidance on the quality, preclinical and clinical aspects of gene transfer medicinal products" (CHMP/BWP/3088/99); regulatory texts on biotechnological products (ICH Q5A to ICH Q5E); regulatory texts on specifications (ICH Q6A and ICH Q6B) and the quality controls required for parenteral preparations as per the European Pharmacopeia (section 7.0).

Example 3. Lentiviral Vector Titration qPCR reactions: HEK 293T cells are seeded in 6-well plates (BD Falcon) in culture medium and incubated for 4 h at 37° C., 5% CO2 in moist atmosphere. Cells are transduced with 3 successive dilutions of lentiviral vector. 72 h post-incubation, cells are harvested and transduced HEK 293T cell pellets are produced. Total genomic DNA from transduced cell-pellets is extracted using a method based on QIAGEN QIAamp DNA mini kit handbook. Proviral quantification is performed using Taqman qPCR. The amplification is performed with the Master Mix (Fermentas Thermo Scientific), the Flap A (CCCAAGAACCCAAGGAACA; SEQ ID NO: 18) and Flap S (AGACAA GATAGAG-GAAGAGCAAAAC; SEQ ID NO: 19) primers and LENTI TM probe (6FAM-AACCATTAGGAGTAGCACCCAC-CAAGG-BBQ; SEQ ID NO: 20). Normalization is performed with the quantification of the actin gene (same Mix, Actine A-CGGTGAGGATCTTCATGAGGTAGT- (SEQ ID NO: 21), Actine S-AACACCCCAGCCATGTACGT- (SEQ ID NO: 22) primers and HUMURA ACT TM probe-6FAM-CCAGCCAGGTCCAGACGCAGGA-BBQ- (SEQ ID NO: 23). Both reactions are achieved on MasterCycler Ep Realplex S (Eppendorf, 2 min at 50° C., 10 min at 95° C. and 40 cycles of 15 seconds at 95° C. and 1 min at 63° C.). The analysis is performed on MasterCycler Ep Realplex Software.

FACS analyses are then performed.

Example 4. T-Specific Response (Median) in C57Bl/6j Mice with or without Prime-Boost Immunization Animals: Female mice (C57Bl/6J) of four weeks or Sprague Dawley RjHan:SD (Sprague Dawley) female mice of eight weeks were purchased from Janvier Laboratories (France).

The animals were housed in Institute Pasteur animal facility in accordance with Institute regulations on the respect of animal experimentation ethical procedures.

Two groups of 5 mice were intramuscularly immunized according to a prim-boost strategy (P/B):
(i) the first one with $7 \times 10^7$ TU of lentiviral vectored HBV construct HBV-3 of the invention in prime and $7 \times 10^7$ TU of lentiviral vectored HBV construct HBV-3 of the invention in boost;

(ii) the second group with 7×10⁶ TU of lentiviral vectored HBV construct HBV-3 in prime and 7×10⁶ TU of lentiviral vectored HBV construct HBV-3 in boost. In these two groups, 7 weeks separate the prime and the boost injections.

Two other mice groups were intramuscularly immunized according to a prime injection strategy (P):
(i) the first one (2 mice) with 7×10⁷ TU of lentiviral vectored HBV construct HBV-3;
(ii) the second group (5 mice) with 7×10⁶ TU of lentiviral vectored HBV construct HBV-3.

Control mice were intramuscularly injected with PBS-lactose.

The lentivectors in which the HBV-3 construct expression of the invention is driven by a promoter (e.g., β2m or MHCI). 15 days after prime immunization, or after boost immunization for the two groups concerned, the specific T-cell responses can be monitored in mice splenocytes by IFN-γ ELISPOT.

Ninety-six-well tissue culture plates (Millipore) are coated overnight at 4° C. with 50 µl/well of 5 µg/ml anti-mouse IFN-γ mAb (Mouse IFN-γ Elispot pair; BD Biosciences Pharmingen). The plates are washed three times with 200 µl DPBS/well and blocked with 200 µl/well of DPBS/10% fetal bovine serum for 2 h at 37° C. The plates are washed three times with 200 µl DPBS/well. Splenocytes are added to the plates in triplicate at 2.5, 4.1, or 5.1×10⁵ cells/well and stimulated with 2 µg/ml of stimulatory peptides (specific to the antigen), concanavalin A (5 µg/ml; source), or culture medium alone. The plates are incubated for 18 h at 37° C. and then rinsed three times with 200 µl/well of DPBS/0.05% Tween 20 and three times with 200 µl/well of DPBS. For detection, 50 µl/well of 2 µg/ml anti-mouse IFN-γ-biotinylated monoclonal antibody (BD Pharmingen) are added 2 h at room temperature. Plates are washed and 100 µl/well of streptavidin-alkaline phosphatase (Roche) diluted 1:2000 in Dulbecco's PBS for 90 min at room temperature. After washing the plates, spots (IFN-γ-secreting cells) are visualized by adding 60 µl/well of BCIP/NBT solution (Sigma). Plates are incubated for 15-30 min at room temperature until blue spots develop and are thoroughly washed with running tap water and air-dried for 24 h. Finally, the spots were counted using a Bioreader 2000 (Biosys).

The cumulated immune response and diversity of the T immune response measured in this experiment is represented in FIG. 2. FIG. 2 moreover illustrates the proportion of immune response for each antigen in the cumulated results.

The results obtained demonstrate that a significant immune response is obtained compared to the control group when injected (in both prime (P) and prime/boost (P/B) groups) with the vectors at the dose of 7×10⁷ TU.

An improved immune response is obtained compared to the control group when injected with vectors comprising the construction of the invention, at the dose of 7×10⁶ TU according to a prime/boost strategy (P/B).

Better immune response results are obtained when injected at a dose of 7×10⁷ TU compared to the dose of 7×10⁶ TU, both with the (P/B) and (P) strategies.

At similar doses (i.e. 7×10⁷ TU or 7×10⁶ TU), the immune response induced by vectors administered according to a prime-boost strategy (P/B) is significantly higher than the immune response induced by the vectors administered according to a prime strategy (P).

Said induced immune response is more particularly strong against Core, PolA, XC, EnvC and VLP in the group of mice immunized according to a prim-boost strategy (P/B) with 7×10⁷ TU.

The induced immune response is more particularly strong against XC and EnvC in the group of mice immunized according to a prim-boost strategy (P/B) with 7×10⁶ TU.

The induced immune response is more particularly strong against Core, PolA, PolC and XA, in particular against Core in the group of mice immunized according to a prim strategy (P) with 7×10⁷ TU.

Example 5. HBV Antigens

HBV therapeutic vaccine, designed for use in the general population, needs to be based on numerous epitopes restricted by multiple HLA types in order to provide acceptable levels of population coverage.

To induce multispecific CTL responses, which are key to resolution of HBV infection, a lentiviral vector carrying envelop surface antigen, polymerase, HBX protein and HBV consensus core of genotypes A and C antigens was constructed.

HBV core protein based chimeric VLP can be constructed to stimulate multivalent immunity against surface antigen and HBV core, since, immune responses specific for both HBV core Ag and HBV surface Ag play an important role in controlling HBV infection. HBV surface Ag-specific antibodies mediate elimination of virions at an early stage of infection and prevent the spread of virus. The chimeric VLP can be constructed by inserting the immunodominant, antibody-binding determinant of HBV surface Ag into the HBV core Ag.

More than a thousand Hepatitis genotype A and genotype C antigen sequences were collected from HBV database, HBVdb, (see online HBVdb/HBVdbIndex) and the genotype-specific antigen consensus sequences were obtained by performing multiple sequence alignments.

CLUSTALW, an alignment software product, (see HBVdb/HBVdbDataset?seqtype=2) was used to create multiple alignments needed to generate a consensus sequence.

Highly conserved HBV-derived peptides that bind multiple HLA class I and class II alleles with high affinity are recognized as CTL epitopes in acutely infected patients are selected (Reignat et al., J. Exp. Med. 195:1089-1101 (2002); Mizukoshi et al., J. Immunol. 173:5863-5871 (2004); Su et al., Proc Natl Acad Sci USA 1997; 94:8744-8749; Desmond et al., Antiviral Therapy 2007; 13:161-175; Bertoni et al., J Clin Invest. 1997 Aug. 1; 100(3):503-13; Nayersina et al., J Immunol. 1993 May 15; 150(10):4659-71; Rehermann et al., J Clin Invest. 1996 April 1; 97(7):1655-65; Kakimi et al., J Virol. 2002 September; 76(17):8609-20; Mizukoshi et al., J Immunol. 2004 Nov. 1; 173(9):5863-71; Depla et al., J Virol. 2008 January; 82(1):435-50; Ding et al., Hepatology. 2009 May; 49(5):1492-502).

The order of the HLA epitopes was selected to distribute epitopes throughout the construct. The construct is shown in FIG. 1.

To avoid toxic long-term drug treatment or to support only partially effective antiviral therapy, LV based HBV therapeutic vaccine can augment the patient's immune system effectually to combat and control the virus.

Inclusion of key viral antigens ensures effective stimulation of T-cell responses—in addition activation of a humoral immune response.

The HBV therapeutic vaccine can break tolerance and induce T-cells infiltration into the liver. The multi-antigen vaccine construct designed to elicit multi-specific, multi-functional cellular and humoral responses, mimicking clearance of natural HBV infection. HBV core based chimeric VLP can act as an adjuvant. Since it can be used without adjuvant, it can eliminate the majority of the adverse reactions.

Example 6. Preclinical Evaluation

Animal Efficacy Studies:

HBV transgenic mice (HBV-Tg) of both genders will be used for the proposed work. They will first be subjected to a ⅓ partial hepatectomy to assess virus replication levels in the liver prior to vaccination.

After the HBV-Tg mice recover from hepatectomy, they will be vaccinated once, and three weeks later, vaccinated again (boosted).

The vaccine is composed of a lentivirus vector expressing a combination of HBV antigens.

Three weeks after the boost, the mice will be retro-orbitally bled and tested for the presence of HBV DNA in blood by real-time qPCR.

Serum collected prior to immunization, and three weeks after the boost will be tested for levels of HBV associated biomarkers, preferably HBsAg, anti-HBs and ALT.

At the end of the observation period, mice will be euthanized and intrahepatic templates supporting HBV replication will be analyzed and quantified by Southern blot hybridization.

The presence of integrated HBV DNA will also be assessed. Livers will be stained for HBV associated biomarkers, preferably HBsAg, anti-HBs and ALT.

The results will be compared between prior and after vaccination in test and control groups.

As a control for these studies, nontransgenic littermates will also be used. Another two groups of mice will be vaccinated as described above, but will also be injected i,p. with anti-PD-1 at the time of initial immunization and again at the time of boost.

Toxicity studies will be performed using the maximal injectable volume in rat, 200 μl in the left plus 200 μl in the right hind limb muscle, via intramuscular injection. Hence, toxicity of the maximal feasible dose will be assessed using the clinical chosen route. Intravenous injection (slow infusion in the caudal vein) using the same total volume (400 μl) will be performed in other animals to assess systemic exposure. The dose corresponding to this volume is not yet known as the titer of the batches (expressed in TU mL-1) varies from one batch to another. In case of an adverse event considered as significant occurs, a second, lower, dose will be assessed. This lower dose will be ⅕ of the MAD to be consistent with i. The preclinical data gathered on the therapeutic HIV vaccines and other preclinical development plans; ii. the sensitivity of the methods used for vector titration and during injection. Following guidelines recommendations ("The WHO guidelines on nonclinical evaluation of vaccines"), groups will be constituted by 10 males and 10 females plus control groups (control to be determined as the final composition of the vectors is to be defined) except for the local tolerance study during which 5 animals/sex/group are planned. Toxicity following IV injection will be assessed without assessment of local tolerance Intramuscularly (the clinical route), two sacrifice dates are planned: at day 4 for interim sacrifice to assess local tolerance (at the injection site) and at day 15 and day 47 for the terminal sacrifice with an ELISPOT to assess immunogenicity after HBV-3 injection. Animals injected intravenously will be sacrificed only at D15 and no ELISPOT will be performed.

Assessment of toxicity will be performed by monitoring the mortality, clinical signs and body weight (once a day), food consumption (once a week), body temperature (before injection, 6 h post-injection then once a day until day 5 then once every 2 days), hepatic enzymes (ASAT, ALAT, on day 2). Microscopic examination of the liver will be performed after terminal sacrifice.

Studies have been designed to assess the biodistribution, shedding and persistence of the integrated vectors sequences of the injected lentiviral vectors.

Each of the lentiviral vaccines will be injected at the maximal achievable dose in Sprague-Dawley rats, using the clinical chosen route, i.e. intramuscular injection. Sacrifices of 5 males+5 females will be performed at days 3, 21, 33 and 56 days; to be consistent with data previously gathered on the THV01 therapeutic HIV vaccines and other lentiviral vectors developed by the Applicant. Indeed, similar studies were performed on the THV01 vaccines, therapeutic HIV vaccines with similar vector's design but encoding a different antigen. Significant positive signals were detected only at the injection site, the draining lymph nodes and the spleen at days 4 and 21. Residual test items target sequences were found at Day 33 and 56 but results not significantly different from controls.

Blood, urine and faeces will be collected one day before injection, and during 3 days post injection to assess vector' shedding at several late time points. This will be performed following RNA extraction on these samples.

The biodistribution studies described above will enable to gain data on the biodistribution of integrated vector.

The biological response induced by the HBV-3 lentiviral vector will be measured by quantifying the generated T-cell mediated immune response by ELISPOT IFN-γ assay. Indeed, the expected efficacy of these vaccines relies on the induction of a strong, diverse and long lasting T-cell immune response. Hence, rather than generating "non-clinical evidence supporting the potential clinical effect", "the related biological effect" will be assessed.

The humoral response against HBV-3 vector will consist mostly in antibodies generated against the VSV envelope proteins used for vectors' pseudotyping. This humoral response is therefore considered as an "unwanted immunogenicity".

The cellular immune response will be evaluated by performing ELISPOT that will measure the number of specific effector T-lymphocytes via IFN-γ secretion. Lentiviral vectors will be injected into animals, then their splenocytes isolated and the immune response assessed against a panel of HBV peptides representatives of the epitopes as indicated here-above. These studies will enable evaluation of the efficient dose.

Finally, characterisation of the immune response will be performed by quantifying the CD4+ T cell and the CD8+ T cell response.

Pre-existing immunity and induction of an immune response to the VSV-G protein may result in a decreased efficacy of the vaccination. Indeed, if host's antibodies bind to the HBV-3 vector particles, less DCs will be transduced by these particles, which might lead to the induction of immune responses of lower magnitude.

To assess this risk, both the presence of pre-existing anti-VSV-G antibodies and the induction of these antibodies after each vaccination was or will be assessed:

The prevalence of anti-VSV-G antibodies has been assessed using human sera and an ELISA developed in-house. Briefly, vectors pseudotyped by the VSV-G serotypes but encoding the luciferase were incubated at several dilutions with approximately 100 human sera. The percentage of transduced cells was quantified by FACS after addition of luciferine: the higher the percentage, the less neutralizing activity. This neutralizing activity is considered to be due to antibodies against the specific envelope serotype; hence indirect assessment of the prevalence is performed. Results showed that a negligible percentage of the patients display pre-existing anti-VSV-G antibodies. Such an evaluation might be relevant to be performed in clinic if trials are held in regions where the prevalence of VSV infection is higher than Europe.

ELISA will be performed on blood samples taken from rats injected with the preclinical batches of the vectors and will assess the humoral response specific to each of the serotypes.

Local tolerance will be assessed during the acute toxicity study by macroscopic and post-mortem microscopic observation of the injection site.

The expected effect of the HBV-3 treatment is the induction of a cellular immune response. This will lead to elimination of the infected cells as well as those transduced by the HBV-3 vector from the host.

As the vectors will be injected intramuscularly and not systemically, the risk of germline transmission is reduced.

A phase I/II study will be carried out in chronically infected patients.

In addition to the primary endpoints, the cellular immune response elicited by the vaccine candidate will be studied by monitoring the cellular immune response by cytokines and integrins quantification.

The invention claimed is:

1. A lentiviral vector encoding:
   - at least one Hepatitis B virus (HBV) envelop surface of genotype A antigen, genotype C antigen or genotypes A and C antigen,
   - at least one polymerase of genotype A antigen, genotype C antigen or genotypes A and C antigen,
   - at least one HBX protein of genotype A antigen, genotype C antigen or genotypes A and C antigen,
   - at least one HBV consensus core of genotype A antigen, genotype C antigen or genotypes A and C antigen, and
   - at least one HBV consensus core MHCI and/or MHCII epitope of genotype A antigen, genotype C antigen or genotypes A and C antigen.

2. The lentiviral vector of claim 1, wherein the lentiviral vector encodes at least the amino acid sequence of SEQ ID NO:24.

3. The lentiviral vector of claim 1, wherein the vector encodes at least the amino acid sequence of SEQ ID NO:25.

4. The lentiviral vector according to claim 1, wherein the lentiviral vector encodes at least the amino acid sequence of SEQ ID NO:24 and at least the amino acid sequence of SEQ ID NO:25.

5. The lentiviral vector according to claim 1, wherein the lentiviral vector comprises a β2-microglobulin promoter.

6. The lentiviral vector according to claim 1, wherein the lentiviral vector is a DNA.

7. A lentiviral vector particle encoding:
   - at least one Hepatitis B virus (HBV) envelop surface of genotype A antigen, genotype C antigen or genotypes A and C antigen,
   - at least one polymerase of genotype A antigen, genotype C antigen or genotypes A and C antigen,
   - at least one HBX protein of genotype A antigen, genotype C antigen or genotypes A and C antigen,
   - at least one HBV consensus core of genotype A antigen, genotype C antigen or genotypes A and C antigen, and
   - at least one HBV consensus core MHCI and/or MHCII epitope of genotype A antigen, genotype C antigen or genotypes A and C antigen.

8. The lentiviral vector particle according to claim 7, wherein the vector encodes the amino acid sequence of SEQ ID NO:24.

9. The lentiviral vector particle according to claim 7, wherein the vector encodes the amino acid sequence of SEQ ID NO:25.

10. The lentiviral vector particle according to claim 7, wherein the vector encodes at least the amino acid sequence of SEQ ID NO:24 and at least the amino acid sequence of SEQ ID NO:25.

11. The lentiviral vector particle according to claim 7, wherein the lentiviral vector particle comprises a functional lentiviral integrase protein.

12. The lentiviral vector particle according to claim 7, wherein the lentiviral vector particle comprises a vesicular stomatitis virus glycoprotein.

13. The lentiviral vector particle according to claim 7, wherein the lentiviral vector particle comprises HIV-1 subtype D Gag and Pol proteins.

14. An isolated cell comprising the lentiviral vector according to claim 1.

15. A composition comprising a lentiviral vector according to claim 1.

16. An isolated cell comprising the lentiviral vector particle according to claim 7.

17. A composition comprising a lentiviral vector according to claim 7.

* * * * *

```
                          SEQUENCE LISTING

<160> NUMBER OF SEQ ID NOS: 26

<210> SEQ ID NO 1
<211> LENGTH: 220
<212> TYPE: DNA
<213> ORGANISM: Homo sapiens

<400> SEQUENCE: 1
attggggagt cccagccttg gggattcccc aactccgcag tttcttttct ccctctccca      60
acctatgtag ggtccttctt cctggatact cacgacgcgc acccagttct cactcccatt     120
gggtgtcggg tttccagaga agccaatcag tgtcgtcgcg gtcgcggttc taaagtccgc     180
acgcacccac cgggactcag attctcccca gacgccgagg                           220

<210> SEQ ID NO 2
<211> LENGTH: 197
<212> TYPE: DNA
<213> ORGANISM: Homo sapiens

<400> SEQUENCE: 2
ggggaggcgc agcgttgggg attccccact cccctgagtt tcacttcttc tcccaacttg      60
tgtcgggtcc ttcttccagg atactcgtga cgcgtcccca cttcccactc ccattgggta     120
ttggatatct agagaagcca atcagcgtcg ccgcggtccc agttctaaag tccccacgca     180
cccacccgga ctcagag                                                    197

<210> SEQ ID NO 3
<211> LENGTH: 216
<212> TYPE: DNA
<213> ORGANISM: Homo sapiens

<400> SEQUENCE: 3
cactggggag gcgccgcgtt gaggattctc cactcccctc agtttcactt cttctcccaa      60
cctgcgtcgg gtccttcttc ctgaatactc atgacgcgtc cccaattccc actcccattg     120
ggtgtcgggt tctagagaag ccaatcagcg tctccgcagt cccggtctaa agtccccagt     180
cacccacccg gactcagatt ctccccagac gccgag                               216

<210> SEQ ID NO 4
<211> LENGTH: 205
<212> TYPE: DNA
<213> ORGANISM: Homo sapiens

<400> SEQUENCE: 4
taagaactgc tgattgctgg gaaactctgc agtttcccgt tcctctcgta acctggtcat      60
```

```
gtgtccttct tcctggatac tcatgacgca gactcagttc tcattcccaa tgggtgtcgg      120
gtttctagag aagccaatca gcgtcgccac gactcccgac tataaagtcc ccatccggac      180
tcaagaagtt ctcaggactc agagg                                            205
```

<210> SEQ ID NO 5
<211> LENGTH: 252
<212> TYPE: DNA
<213> ORGANISM: Homo sapiens

<400> SEQUENCE: 5

```
aggcccgag gcggtgtctg gggttggaag gctcagtatt gagaattccc catctcccca       60
gagtttctct ttctctccca acccgtgtca ggtccttcat cctggatact cataacgcgg     120
ccccatttct cactcccatt gggcgtcgcg tttctagaga agccaatcag tgtcgccgca     180
gttcccaggt tctaaagtcc cacgcacccc gcgggactca tattttccc agacgcggag      240 gttggggtca tg                                                         252
```

<210> SEQ ID NO 6
<211> LENGTH: 192
<212> TYPE: DNA
<213> ORGANISM: Homo sapiens

<400> SEQUENCE: 6

```
aacatcacga gactctaaga aaaggaaact gaaaacggga aagtccctct ctctaacctg      60
gcactgcgtc gctggcttgg agacaggtga cggtccctgc gggccttgtc ctgattggct     120
gggcacgcgt ttaatataag tggaggcgtc gcgctggcgg gcattcctga agctgacagc     180
attcgggccg ag                                                         192
```

<210> SEQ ID NO 7
<211> LENGTH: 33
<212> TYPE: DNA
<213> ORGANISM: Artificial Sequence
<220> FEATURE:
<223> OTHER INFORMATION: Synthetic PCR primer

<400> SEQUENCE: 7

```
cttactagtt ggaagggcta attcactccc aac                                    33
```

<210> SEQ ID NO 8
<211> LENGTH: 32
<212> TYPE: DNA
<213> ORGANISM: Artificial Sequence
<220> FEATURE:
<223> OTHER INFORMATION: Synthetic PCR primer

<400> SEQUENCE: 8

```
cattctagaa ctgctagaga ttttccacac tg                                     32
```

<210> SEQ ID NO 9
<211> LENGTH: 42
<212> TYPE: DNA
<213> ORGANISM: Artificial Sequence
<220> FEATURE:
<223> OTHER INFORMATION: Synthetic PCR primer

<400> SEQUENCE: 9

```
taccccgggc catggcctcc aaaaaagcct cctcactact tc                          42
```

<210> SEQ ID NO 10

```
<211> LENGTH: 44
<212> TYPE: DNA
<213> ORGANISM: Artificial Sequence
<220> FEATURE:
<223> OTHER INFORMATION: Synthetic PCR primer

<400> SEQUENCE: 10
actcccgggt aattttttt atttatgcag aggccgaggc cgcc                        44

<210> SEQ ID NO 11
<211> LENGTH: 35
<212> TYPE: DNA
<213> ORGANISM: Artificial Sequence
<220> FEATURE:
<223> OTHER INFORMATION: Synthetic PCR primer

<400> SEQUENCE: 11
tacacgcgtg gagttccgcg ttacataact tacgg                                 35

<210> SEQ ID NO 12
<211> LENGTH: 39
<212> TYPE: DNA
<213> ORGANISM: Artificial Sequence
<220> FEATURE:
<223> OTHER INFORMATION: Synthetic PCR primer

<400> SEQUENCE: 12
cgtggatccg atcgcggtgt cttctatgga ggtcaaaac                             39

<210> SEQ ID NO 13
<211> LENGTH: 34
<212> TYPE: DNA
<213> ORGANISM: Artificial Sequence
<220> FEATURE:
<223> OTHER INFORMATION: Synthetic PCR primer

<400> SEQUENCE: 13
gccggcgcgc cgagaaaccc tgcagggaat tccc                                  34

<210> SEQ ID NO 14
<211> LENGTH: 41
<212> TYPE: DNA
<213> ORGANISM: Artificial Sequence
<220> FEATURE:
<223> OTHER INFORMATION: Synthetic PCR primer

<400> SEQUENCE: 14
cgtggatccg atcgctcggc ccgaatgctg tcagcttcag g                          41

<210> SEQ ID NO 15
<211> LENGTH: 517
<212> TYPE: DNA
<213> ORGANISM: Artificial Sequence
<220> FEATURE:
<223> OTHER INFORMATION: Synthetic Amplified B2m promoter sequence

<400> SEQUENCE: 15
gagaaaccct gcagggaatt ccccagctgt agttataaac agaagttctc cttctgctag      60
gtagcattca aagatcttaa tcttctgggt ttccgttttc tcgaatgaaa aatgcaggtc     120
cgagcagtta actggcgggg gcaccattag caagtcactt agcatctctg gggccagtct     180
gcaaagcgag ggggcagcct taatgtgcct ccagcctgaa gtcctagaat gagcgcccgg     240
tgtcccaagc tggggcgcgc acccagatc ggagggcgcc gatgtacaga cagcaaactc      300
acccagtcta gtgcatgcct tcttaaacat cacgagactc taagaaaagg aaactgaaaa     360
```

```
cgggaaagtc cctctctcta acctggcact gcgtcgctgg cttggagaca ggtgacggtc    420
cctgcgggcc ttgtcctgat tggctgggca cgcgtttaat ataagtggag gcgtcgcgct    480
ggcgggcatt cctgaagctg acagcattcg ggccgag                             517
```

<210> SEQ ID NO 16
<211> LENGTH: 47
<212> TYPE: DNA
<213> ORGANISM: Artificial Sequence
<220> FEATURE:
<223> OTHER INFORMATION: Synthetic PCR primer

<400> SEQUENCE: 16

```
atgcatgcgt cgacctcgag ttaatcctca tcctgtctac ttgccac                  47
```

<210> SEQ ID NO 17
<211> LENGTH: 65
<212> TYPE: DNA
<213> ORGANISM: Artificial Sequence
<220> FEATURE:
<223> OTHER INFORMATION: Synthetic PCR primer

<400> SEQUENCE: 17

```
gcatgcatcg gccggggcgg cgactggtga gaggccacca tgggtgcgag agcgtcagta    60
ttaag                                                                65
```

<210> SEQ ID NO 18
<211> LENGTH: 19
<212> TYPE: DNA
<213> ORGANISM: Artificial Sequence
<220> FEATURE:
<223> OTHER INFORMATION: Synthetic PCR primer

<400> SEQUENCE: 18

```
cccaagaacc caaggaaca                                                 19
```

<210> SEQ ID NO 19
<211> LENGTH: 25
<212> TYPE: DNA
<213> ORGANISM: Artificial Sequence
<220> FEATURE:
<223> OTHER INFORMATION: Synthetic PCR primer

<400> SEQUENCE: 19

```
agacaagata gaggaagagc aaaac                                          25
```

<210> SEQ ID NO 20
<211> LENGTH: 27
<212> TYPE: DNA
<213> ORGANISM: Artificial Sequence
<220> FEATURE:
<223> OTHER INFORMATION: Synthetic probe

<400> SEQUENCE: 20

```
aaccattagg agtagcaccc accaagg                                        27
```

<210> SEQ ID NO 21
<211> LENGTH: 24
<212> TYPE: DNA
<213> ORGANISM: Artificial Sequence
<220> FEATURE:
<223> OTHER INFORMATION: Synthetic PCR primer

<400> SEQUENCE: 21
cggtgaggat cttcatgagg tagt                                          24

<210> SEQ ID NO 22
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 22
aacaccccag ccatgtacgt                                               20

<210> SEQ ID NO 23
<211> LENGTH: 22
<212> TYPE: DNA
<213> ORGANISM: Artificial Sequence
<220> FEATURE:
<223> OTHER INFORMATION: Synthetic probe

<400> SEQUENCE: 23
ccagccaggt ccagacgcag ga                                            22

<210> SEQ ID NO 24
<211> LENGTH: 1049
<212> TYPE: PRT
<213> ORGANISM: Hepatitis B virus

<400> SEQUENCE: 24

Met Trp Pro Ala Ala Asn Gln Val Gly Val Gly Ala Phe Gly Pro Gly
1               5                   10                  15

Leu Gly Ser Met Gln Trp Asn Ser Thr Ala Phe His Gln Ala Leu Gln
            20                  25                  30

Asp Pro Arg Val Arg Gly Leu Gly Ser Ser Ile Ser Ala Arg Thr Gly
        35                  40                  45

Asp Pro Val Gly Ser Val Leu Gln Ala Gly Phe Phe Leu Leu Thr Arg
    50                  55                  60

Ile Leu Thr Ile Pro Gln Ser Leu Asp Ser Trp Trp Thr Ser Leu Asn
65                  70                  75                  80

Phe Leu Gly Gly Ser Pro Val Cys Leu Gly Gln Asn Ser Gln Ser Pro
                85                  90                  95

Thr Ser Asn His Ser Pro Thr Ser Cys Pro Pro Ile Cys Pro Gly Tyr
            100                 105                 110

Arg Trp Met Cys Leu Arg Arg Phe Gly Ser Ile Ile Phe Leu Phe Ile
        115                 120                 125

Leu Leu Leu Cys Leu Ile Phe Leu Leu Val Leu Leu Asp Tyr Gln Gly
    130                 135                 140

Met Leu Gly Ser Cys Thr Thr Pro Ala Gln Gly Asn Ser Met Phe Pro
145                 150                 155                 160

Ser Cys Cys Cys Thr Lys Pro Thr Asp Gly Asn Gly Ser Ile Pro Ser
                165                 170                 175

Ser Trp Ala Phe Ala Gly Ser Arg Phe Ser Trp Leu Ser Leu Leu Val
            180                 185                 190

Pro Phe Val Gln Trp Phe Val Gly Leu Ser Pro Thr Val Trp Leu Ser
        195                 200                 205

Ala Ile Trp Met Met Trp Tyr Trp Gly Pro Ser Leu Tyr Ser Ile Val
    210                 215                 220

Ser Pro Phe Ile Pro Leu Leu Pro Ile Phe Phe Cys Leu Trp Val Tyr
225                 230                 235                 240

```
Ile Gly Ser Asn Val Ser Ile Pro Trp Thr His Lys Val Gly Asn Phe
            245                 250                 255
Thr Gly Leu Tyr Ser Ser Thr Val Pro Ile Gly Ser Val Gly Pro Leu
        260                 265                 270
Thr Val Asn Glu Lys Arg Arg Leu Lys Leu Ile Gly Ser Arg His Tyr
    275                 280                 285
Leu His Thr Leu Trp Lys Ala Gly Ile Leu Tyr Lys Gly Ser Thr Pro
290                 295                 300
Ala Arg Val Thr Gly Val Phe Gly Ser Glu Ser Arg Leu Val Val
305                 310                 315                 320
Asp Phe Ser Gln Phe Ser Arg Gly Ile Thr Arg Val Ser Trp Pro Lys
                325                 330                 335
Phe Ala Val Pro Asn Leu Gln Ser Leu Thr Asn Leu Leu Ser Ser Asn
            340                 345                 350
Leu Ser Trp Leu Ser Leu Asp Val Ser Ala Ala Phe Tyr His Ile Pro
        355                 360                 365
Leu His Pro Ala Ala Met Pro His Leu Leu Ile Gly Ser Ser Gly Leu
    370                 375                 380
Ser Arg Tyr Val Ala Arg Leu Gly Ser Leu His Leu Tyr Ser His Pro
385                 390                 395                 400
Ile Val Leu Gly Phe Arg Lys Ile Gly Ser Ala Ile Cys Ser Val
                405                 410                 415
Val Arg Arg Ala Phe Pro His Cys Leu Ala Phe Ser Tyr Met Asp Asp
            420                 425                 430
Val Val Leu Gly Ala Gly Ser Phe Leu Leu Ser Leu Gly Ile His Leu
        435                 440                 445
Gly Ser Lys His Cys Phe Arg Lys Leu Pro Val Asn Arg Pro Ile Asp
    450                 455                 460
Trp Gly Ser Tyr Pro Ala Leu Met Pro Leu Tyr Ala Cys Ile Gln Ala
465                 470                 475                 480
Lys Gln Ala Phe Thr Phe Ser Pro Thr Tyr Lys Ala Phe Leu Ser Gly
                485                 490                 495
Ser Leu Cys Gln Val Phe Ala Asp Ala Thr Pro Thr Gly Trp Gly Leu
            500                 505                 510
Gly Ser Lys Tyr Thr Ser Phe Pro Trp Leu Leu Gly Cys Thr Ala Asn
        515                 520                 525
Trp Ile Leu Arg Gly Thr Ser Phe Val Tyr Val Pro Gly Ser Ser Leu
    530                 535                 540
Tyr Ala Val Ser Pro Ser Val His Leu Ser Leu Arg Gly Leu Pro Val
545                 550                 555                 560
Gly Ser Val Leu His Lys Arg Thr Leu Gly Leu Pro Ala Met Ser Thr
                565                 570                 575
Thr Asp Leu Gly Ser Cys Val Phe Lys Asp Trp Glu Glu Leu Gly Glu
            580                 585                 590
Glu Ile Arg Leu Lys Val Leu Phe Val Leu Gly Gly Cys Arg His Lys
        595                 600                 605
Leu Gly Ser Trp Pro Glu Ala Asn Gln Val Gly Ala Gly Ala Phe Gly
    610                 615                 620
Pro Gly Phe Gly Ser Met Gln Trp Asn Ser Thr Thr Phe His Gln Ala
625                 630                 635                 640
Leu Leu Asp Pro Arg Val Arg Gly Leu Tyr Phe Pro Ala Gly Gly Ser
                645                 650                 655
Ser Ser Gly Gly Ser Thr Ser Leu Asn Phe Leu Gly Gly Ala Pro Thr
```

-continued

```
                660                 665                 670
Cys Pro Gly Gln Gly Ser Cys Thr Ile Pro Ala Gln Gly Thr Ser Met
            675                 680                 685
Phe Pro Ser Cys Cys Cys Thr Lys Pro Ser Asp Gly Asn Cys Thr Cys
        690                 695                 700
Gly Ser Gly Leu Ser Pro Thr Val Trp Leu Ser Val Ile Trp Met Met
705                 710                 715                 720
Trp Tyr Trp Gly Pro Ser Leu Tyr Asn Ile Leu Ser Pro Phe Leu Pro
                725                 730                 735
Leu Leu Pro Ile Phe Phe Cys Leu Trp Val Tyr Ile Gly Ser Asn Val
            740                 745                 750
Ser Ile Pro Trp Thr His Lys Val Gly Asn Phe Thr Gly Leu Tyr Ser
        755                 760                 765
Ser Thr Val Pro Val Gly Ser Leu His Leu Tyr Ser His Pro Ile Ile
770                 775                 780
Leu Gly Phe Arg Lys Ile Gly Ser Lys Gln Cys Phe Arg Lys Leu Pro
785                 790                 795                 800
Val Asn Arg Pro Ile Asp Trp Gly Ser Lys Gln Ala Phe Thr Phe Ser
                805                 810                 815
Pro Thr Tyr Lys Ala Phe Leu Cys Gly Ser Leu Cys Gln Val Phe Ala
            820                 825                 830
Asp Ala Thr Pro Thr Gly Trp Gly Leu Gly Ser Ala Ala Asn Trp Ile
        835                 840                 845
Leu Arg Gly Thr Ser Phe Val Tyr Val Pro Gly Ser Val Leu His Lys
850                 855                 860
Arg Thr Leu Gly Leu Ser Ala Met Ser Thr Thr Asp Leu Gly Ser Cys
865                 870                 875                 880
Leu Phe Lys Asp Trp Glu Glu Leu Gly Glu Ile Arg Leu Met Ile
                885                 890                 895
Phe Val Leu Gly Gly Cys Arg His Lys Leu Gly Ser Met Asp Ile Asp
            900                 905                 910
Pro Tyr Lys Glu Phe Gly Ala Thr Val Glu Leu Leu Ser Phe Leu Pro
        915                 920                 925
Ser Asp Phe Phe Pro Ser Val Arg Asp Leu Gly Ser Ala Leu Glu Ser
930                 935                 940
Pro Glu His Cys Ser Pro His His Thr Ala Leu Arg Gln Ala Ile Leu
945                 950                 955                 960
Gly Ser Glu Leu Met Thr Leu Ala Thr Trp Val Gly Ser Ser Arg Asp
                965                 970                 975
Leu Val Val Asn Tyr Val Asn Thr Asn Met Gly Leu Lys Ile Arg Gln
            980                 985                 990
Leu Leu Trp Phe His Ile Ser Cys Leu Thr Phe Gly Arg Glu Thr Val
        995                 1000                1005
Leu Glu Tyr Leu Val Ser Phe Gly Val Trp Ile Arg Thr Pro Pro
1010                1015                1020
Gly Ser Ile Leu Ser Thr Leu Pro Glu Thr Thr Val Val Arg Arg
    1025                1030                1035
Arg Asp Arg Gly Arg Ser Pro Arg Arg Arg Thr
    1040                1045
```

<210> SEQ ID NO 25
<211> LENGTH: 468
<212> TYPE: PRT
<213> ORGANISM: Hepatitis B virus

<400> SEQUENCE: 25

| | | | | | | | | | | | | | | |
|---|---|---|---|---|---|---|---|---|---|---|---|---|---|---|
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Gly Gly
65                  70                  75                  80

Gly Gly Ser Gly Gly Gly Gly Thr Pro Leu Gly Phe Phe Pro Asp His
                85                  90                  95

Gln Leu Asp Pro Ala Phe Gly Ala Asn Ser Asn Asn Pro Asp Trp Asp
            100                 105                 110

Phe Asn Gly Ser Ala Ser Thr Asn Arg Gln Ser Gly Arg Gln Pro Thr
            115                 120                 125

Pro Ile Ser Pro Pro Leu Arg Asp Ser His Pro Gln Met Gln Trp Asn
    130                 135                 140

Ser Thr Ala Phe His Gln Ala Leu Gln Asp Pro Arg Val Arg Gly Leu
145                 150                 155                 160

Tyr Phe Pro Ala Gly Gly Ser Ser Ser Gly Thr Val Asn Pro Ala Pro
                165                 170                 175

Asn Ile Ala Ser His Ile Ser Ser Ile Ser Ala Arg Thr Gly Asp Gly
            180                 185                 190

Ser Cys Lys Thr Cys Thr Thr Pro Ala Gln Gly Asn Ser Met Phe Pro
    195                 200                 205

Ser Cys Cys Cys Thr Lys Pro Thr Asp Gly Asn Cys Thr Cys Ile Pro
    210                 215                 220

Ile Pro Ser Ser Trp Ala Phe Ala Lys Tyr Leu Trp Glu Trp Ala Ser
225                 230                 235                 240

Gly Ser Pro Phe Val Gln Trp Phe Val Gly Leu Ala Met Gln Trp Asn
                245                 250                 255

Ser Thr Thr Phe His Gln Ala Leu Leu Asp Pro Arg Val Arg Gly Leu
            260                 265                 270

Tyr Phe Pro Ala Gly Gly Ser Ser Ser Gly Thr Val Asn Pro Val Pro
                275                 280                 285

Thr Thr Ala Ser Pro Ile Ser Ser Ile Phe Ser Arg Thr Gly Asp Gly
        290                 295                 300

Ser Cys Lys Thr Cys Thr Ile Pro Ala Gln Gly Thr Ser Met Phe Pro
305                 310                 315                 320

Ser Cys Cys Cys Thr Lys Pro Ser Asp Gly Asn Cys Thr Cys Ile Pro
            325                 330                 335

Ile Pro Ser Ser Trp Ala Phe Ala Arg Phe Leu Trp Glu Trp Ala Ser
            340                 345                 350

Gly Ser Gly Gly Gly Gly Ser Gly Gly Gly Gly Ser Arg Asp Leu Val
        355                 360                 365

Val Asn Tyr Val Asn Thr Asn Met Gly Leu Lys Ile Arg Gln Leu Leu
    370                 375                 380

Trp Phe His Ile Ser Cys Leu Thr Phe Gly Arg Glu Thr Val Leu Glu
385                 390                 395                 400

Tyr Leu Val Ser Phe Gly Val Trp Ile Arg Thr Pro Pro Ala Tyr Arg

-continued

```
                405                 410                 415

Pro Pro Asn Ala Pro Ile Leu Ser Thr Leu Pro Glu Thr Thr Val Val
            420                 425                 430

Arg Arg Arg Asp Arg Gly Arg Ser Pro Arg Arg Arg Thr Pro Ser Pro
        435                 440                 445

Arg Arg Arg Arg Ser Gln Ser Pro Arg Arg Arg Arg Ser Gln Ser Arg
    450                 455                 460

Glu Ser Gln Cys
465

<210> SEQ ID NO 26
<211> LENGTH: 141
<212> TYPE: PRT
<213> ORGANISM: Artificial Sequence
<220> FEATURE:
<223> OTHER INFORMATION: Synthetic epitope

<400> SEQUENCE: 26

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Gly Ser
            20                  25                  30

Ala Leu Glu Ser Pro Glu His Cys Ser Pro His His Thr Ala Leu Arg
        35                  40                  45

Gln Ala Ile Leu Gly Ser Glu Leu Met Thr Leu Ala Thr Trp Val Gly
    50                  55                  60

Ser Ser Arg Asp Leu Val Val Asn Tyr Val Asn Thr Asn Met Gly Leu
65                  70                  75                  80

Lys Ile Arg Gln Leu Leu Trp Phe His Ile Ser Cys Leu Thr Phe Gly
                85                  90                  95

Arg Glu Thr Val Leu Glu Tyr Leu Val Ser Phe Gly Val Trp Ile Arg
            100                 105                 110

Thr Pro Pro Gly Ser Ile Leu Ser Thr Leu Pro Glu Thr Thr Val Val
        115                 120                 125

Arg Arg Arg Asp Arg Gly Arg Ser Pro Arg Arg Arg Thr
    130                 135                 140
```